US006921531B2

(12) United States Patent
Briesewitz et al.

(10) Patent No.: US 6,921,531 B2
(45) Date of Patent: Jul. 26, 2005

(54) ADMINISTERING BIFUNCTIONAL MOLECULES CONTAINING A DRUG MOIETY AND PRESENTER PROTEIN LIGAND FOR THERAPY

(75) Inventors: Roger Briesewitz, Mountain View, CA (US); Gerald R. Crabtree, Woodside, CA (US); Thomas Wandless, Menlo Park, CA (US); Gregory Thomas Ray, Stanford, CA (US); Kurt William Vogel, Palo Alto, CA (US)

(73) Assignees: The Board of Trustees of the Leland Stanford Junior University, Palo Alto, CA (US); Howard Hughes Medical Institute, Chevy Chase, MD (US)

( * ) Notice: Subject to any disclaimer, the term of this patent is extended or adjusted under 35 U.S.C. 154(b) by 88 days.

(21) Appl. No.: 10/025,936

(22) Filed: Dec. 21, 2001

(65) Prior Publication Data
US 2002/0147133 A1 Oct. 10, 2002

Related U.S. Application Data

(62) Division of application No. 09/316,932, filed on May 21, 1999, now Pat. No. 6,372,712.
(60) Provisional application No. 60/086,451, filed on May 22, 1998.

(51) Int. Cl.$^7$ .................. A61K 38/52; A61K 38/00; C12N 11/02; C07K 1/00; C07K 17/02
(52) U.S. Cl. ................... 424/94.5; 424/94.1; 514/2; 514/9; 435/177; 530/402; 530/812
(58) Field of Search ............ 514/2, 9; 424/94.1, 424/94.5; 435/177; 530/402, 812

(56) References Cited

U.S. PATENT DOCUMENTS

| 5,382,657 A | 1/1995 | Karasiewicz et al. |
| 5,830,462 A | 11/1998 | Crabtree et al. ......... 424/93.21 |
| 5,834,266 A | 11/1998 | Crabtree et al. ......... 435/172.3 |
| 5,840,733 A | 11/1998 | Krantz et al. ............... 514/311 |
| 5,843,440 A | 12/1998 | Pouletty et al. .......... 424/133.1 |
| 5,869,337 A | 2/1999 | Crabtree et al. ......... 435/372.3 |
| 5,871,753 A | 2/1999 | Crabtree et al. ......... 424/280.1 |
| 6,670,348 B1 | 12/2003 | Rosen et al. ............... 514/174 |
| 2002/0045570 A1 | 4/2002 | Rosen et al. .................... 514/2 |

FOREIGN PATENT DOCUMENTS

| WO | 91/01743 | 2/1991 |
| WO | 94/18317 | 8/1994 |
| WO | 95/02684 | 1/1995 |
| WO | 95/05389 | 2/1995 |
| WO | 95/10302 | 4/1995 |
| WO | 96/06111 | 2/1996 |
| WO | 96/12796 | 5/1996 |
| WO | 97/25074 | 7/1997 |
| WO | 97/29372 | 8/1997 |
| WO | 98/00171 | 1/1998 |
| WO | 98/11437 | 3/1998 |
| WO | 98/46270 | 10/1998 |
| WO | WO 98/47916 | 10/1998 |

OTHER PUBLICATIONS

Atwell, John L., et al., "Design and Expression of a Stable Bispecific scFv Dimer With Affinity for Both Glycophorin and N9 Neuraminidase," *Molecular Immunology* (1996) vol. 22, No. (17/18):1301–1302.
Bernstein, Kenneth E., et al., "A Deeply Recessed Active Site in Angiotensin–Converting Enzyme Is Indicated From the Binding Characteristics of Biotin–Spacer–Inhibitor Reagents," *Biochemical and Biophysical Communications* (Feb. 28. 1990) vol. 167, No. (1):310–316.
Bourdouxhe–Honsiaux, Catherine, et al., "Interaction of DNA–Threading Peptide–Amsacrine Conjugates With DNA and Chromatin," *Anti–Cancer Drug Design* (1996) vol. 11:509–525.
Chakraborty, TK., et al., "Design and Synthesis of a Rapamycin–Based High Affinity Binding FKBP12 Ligand," *Chemistry & Biology* (Mar. 1995) vol. 2:157–161.
Crabtree, Gerald R., et al., "Three–Part Inventions: Intracellular Signalling and Induced Proximity," *Elsevier Trends Journal* (Nov. 1996) pp:418–422.
Ho, Steffan N., et al., "Dimeric Ligands Define a Role for Transcriptional Activation Domains In Reinitiation," *Nature* (Aug. 29, 1996) vol. 382, No. (6594):822–826.
Kramer, Werner, et al., "Liver–Specific Drug Targeting by Coupling to Bile Acids," *The Journal of Biological Chemistry* (1992) vol. 267, No. (2): 18598–18604.
Mogre, R.M., et al., "A New Carbene Based Heterbifunctional Reagent: Photochemical Crosslinking of Aldolase," *FEBS Letters* (Sep. 1987) vol. 221, No. (2):408–414.
Mu, Yu., et al., "Biconjugation of Laminin Peptide YIGSR With Poly(Styrene Co–Maleic Acid) Increases Its Antimetastatic Effect on Lung Metastasis of BI6–BL6 Melanoma Cells," *Biochemical and Biophysical Research Communications* (1999) vol. 255:75–79.
Varshavsky, Alexander, "Codominant Interference, Antieffectors, and Multitarget Drugs," *Proc. Natl. Acad. Sci. USA* (Mar. 1998) vol. 95:2094–2099.

(Continued)

*Primary Examiner*—David M. Naff
(74) *Attorney, Agent, or Firm*—Bret E. Field; Bozicevic, Field & Francis LLP

(57) ABSTRACT

Bifunctional molecules and methods for their use in the production of binary or tripartite complexes in a host are provided. The bifunctional molecule is a conjugate of a drug moiety and a presenter protein ligand. The molecular weight of the bifunctional molecule is less than about 5000 daltons. In the methods, an effective amount of the bifunctional molecule is administered to the host. In certain embodiments the bifunctional molecule binds to the presenter protein and a drug target to produce a tripartite complex, while in other embodiments the bifunctional molecule binds to either the presenter protein or the drug target, but not both, to produce a binary complex The subject methods and compositions find use in a variety of therapeutic applications.

23 Claims, 9 Drawing Sheets

OTHER PUBLICATIONS

Varshavsky, Alexander, "Codominance and Toxins: A Path to Drugs of Neatly Unlimited Selectivity," *Proc. Natl. Acad. Sci. USA* (Apr. 1995) vol. 92:3663–3667.

Al–Obeidi, et al., (1990) "Synthesis and Actions of a Melanotropin Conjugate, Ac–[Nle$^4$, Glu(gamma–4'–hydroxyanilide)$^5$, D–Phe$^7$] α–MSH$_{4-10}$–NH$_2$, on Melanocytes and Melanoma Cells In Vitro," *Journal of Pharmaceutical Sciences* vol. 79, No. (6):500–504.

Belshaw, et al., (1996) "Controlling Protein Association and Subcellular Localization with a Synthetic Ligand that Induces Heterodimerazation of Proteins," *Proc. Natl. Acad. Sci. U.S.A.* vol. 93:4604–4607.

Brochu, et al., (1992) "Modes of Action and Inhibitory Activities of New Siderophore–β–Lactam Conjugates that use Specific Iron Uptake Pathways for Entry Into Bacteria," *Antimicrobial Agents and Chemotherapy* vol. 36, No. (10):2166–2175.

Briesewitz, et al., (1999) "Affinity Modulation of Small–Molecule Ligands by Borrowing Endogenous Protein Surfaces," *P.N.A.S* vol. 96, No. (5):1953–1958.

Heath, et al., (1986) "Liposome–Mediated Delivery of Pteridine Antifolates to cells in Vitro: Potency of Methotrexate, and its α and γ Substituents," *Biochimica et Biophysica Acta* vol. 862:72–80.

Holt, et al., (1994) "Structure–Activity Studies of Synthetic FKBP Ligands as Peptidyl–Prolyl Isomerase Inhibitors," *Bioorganic and Medicinal Chemistry Letters* vol. 4, No. (2):315–320.

Luengo, et al. (1994) "Synthesis and Structure–Activity Relationships of Macrocyclic FKBP Ligands," *Bioorganic and Medicinal Chemistry Letters* vol. 4, No. (2):321–324.

Lussow, et al., (1996) "Targeting of Antihapten Antibodies to Activated T Cells via an IL–2–Hapten Conjugate Prolongs Cardiac Graft Survival," *Trasplantation* vol. 62, No. (12):1703–1708.

Maeda, et al., (1997) "Amino Acids and Peptides XXXII: A Biofunctional Poly(Ethylene Glycol) Hybrid of Fibronectin–Related Peptides," *Biochemical and Biophysical Research Communications* vol. 241:595–598.

Zunino, et al., (1984) "Compassion of Antitumor Effects of Daunorubicin Covalently Linked to Poly–L–Amino Acid Carrires," *Eur. J. Cancer Chem. Oncol.* vol. 20, No. (3):421–425.

Kudak et al., "Synthesis and Evaluation of Geldanamycin–Testosterone Hybrids" *Bloorg–Med. Chem., Lett.* 10 (2000) 1303–1306.

ADMINISTERING BIFUNCTIONAL MOLECULES CONTAINING A DRUG MOIETY AND PRESENTER PROTEIN LIGAND FOR THERAPY

CROSS REFERENCE TO RELATED APPLICATIONS

This application is a Divisional of U.S. patent application Ser. No. 09/316,932, filed May 21, 1999 now U.S. Pat. No. 6,372,712,B1 which claims priority to the filing date of the U.S. Provisional Patent Application Ser. No. 60/086,451 filed May 22, 1998, the disclosure of which is herein incorporated by reference.

ACKNOWLEDGMENT

This invention was made with United States Government support under Grant No. CA39612 awarded by National Institutes of Health. The United States Government has certain rights in this invention.

INTRODUCTION

1. Technical Field

The field of this invention is pharmacology.

2. Background of the Invention

Any chemical agent that affects any process of living is a drug. Drugs are a critical tool for health care practitioners, as they are used in the prevention, diagnosis and treatment of disease. Because of their criticality to the health care profession, annual world investment into the research and development of new chemical agents with therapeutic potential reaches into the billions of dollars. As a result, a large number of drugs have been developed to date and new chemical agents having potential therapeutic utility are frequently discovered. Chemical agents that find, or have found, use as drugs include naturally occurring and synthetic small molecules, as well as larger molecules, such as proteinaceous compounds.

Most small molecule drugs cause a pharmacological effect by binding to a target protein and altering the pharmacological activity of the target in some way. For a given small molecule drug, it is desirable that the drug have at least one of high affinity and specificity for its target. If a small molecule has high affinity for its target, it is characterized by having good binding to its target. If a small molecule has specificity for its target, it is characterized by having differential affinity between its target and other, non-target proteins. Besides displaying high affinity and/or specificity, a given small molecule should be selective with respect to the cell or tissue in which it affects a biological activity. Selectivity will assure that the drug target will be affected by the drug only in cells involved in the disease process.

Screens for small molecule drugs rarely identify high affinity ligands, low affinity ligands with high specificity or selective ligands. Much more often, compounds are identified that have biological activity but with relatively low affinity and low specificity for their targets. Furthermore, identified compounds usually lack selectivity for their targets with respect to cell or tissue type. Because of this low affinity, specificity, or selectivity or combination thereof, these identified ligands never find clinical use.

As such, of great interest to the pharmaceutical industry and related fields would be the development of a method for increasing at least one of the affinity, specificity and selectivity of these previously identified biologically active agents, such that agents that otherwise lack sufficient affinity and/or specificity nonetheless could find clinical utility.

Relevant Literature

Patent publications of interest include: WO 91/01743; WO 94/18317; WO 95/02684; WO 95/10302; WO 96/06111; WO 96/12796; WO 96/13613; WO 97/25074; WO 97/29372; WO 98/11437; WO 98/47916; U.S. Pat. Nos. 5,830,462; 5,843,440; and 5,871,753. References of interest include: Briesewitz et al., Proc. Nat'l Acad. Sci. USA (March 1999) 96: 1953–1958; Clardy, Proc. Nat'l Acad. Sci. USA (March 1999) 1826–1827; Crabtree & Schreiber, Elsevier Trends Journal (November 1996) 418–422; Spencer et al., Curr. Biol. (July 1996) 6:839–847; Spencer et al., Science (1993) 262: 1019; Chakraborty et al., Chem. & Biol. (March 1995) 2:157–161; Ho et al., Nature (1996) 382: 822; Riviera et al., Nature Medicine (1996) 2: 1028; Klemm et al., Current Biology (1997) 7: 638; Belshaw et al., Proc. Nat'l. Acad. Sci. USA (1996) 93: 4604; Livnah et al., Science (1996) 273: 464; Johnson et al., Chemistry and Biology, (1997) 4: 939; Garboczi et al., Nature (1996) 384:134; Kissenger et al., Nature (1995) 378:641; Griffith et al., Cell (1995) 82: 507; Choi et al., Science (1996) 273:239. Also of interest are Kramer et al., J. Biol. Chem. (1992) 267:18598–18604; and Varshavsky, Proc. Nat'l Acad. Sci. USA (March 1998) 95: 2094–2099; Varshavsky, Proc. Nat'l Acad. Sci. USA (April 1995) 92:3663–3667; and Mu et al., Biochem. Biophys. Res. Comm. (1999)255:75–79.

SUMMARY OF THE INVENTION

Bifunctional molecules capable of producing at least a binary complex with a host endogenous presenter protein are provided. In the subject methods, a bifunctional molecule is synthesized by covalently linking an endogenous presenter protein ligand to a drug moiety, either directly or through a linking group. An effective amount of a bifunctional molecule is administered to the host, where the bifunctional molecule binds to the endogenous presenter protein to produce the binary complex. The resultant binary complex modulates (e.g. enlarges) the target binding surface area of the drug moiety, i.e. the surface area available for binding with the target, in a manner such that at least one of enhanced affinity, specificity or selectivity are observed as compared to that observed with the free drug.

In one embodiment where the binary complex results in enhanced affinity, a tripartite complex is produced in which binding interactions are present between the presenter and target as well as the drug moiety and target. In a second embodiment where the binary complex results in enhanced specificity, delivery of the drug as a bifunctional molecule results in differential affinity with respect to its potential targets such that the drug moiety binds more to its desirable target than to its undesirable targets as compared to a free drug control situation, e.g. where tripartite complexes produced between the binary complex and undesired targets are characterized by the presence of unfavorable interactions while tripartite complexes produced between the binary complex and the desired target are characterized by the presence of no interactions, neutral interactions or favorable interactions. In a third embodiment where the binary complex results in enhanced selectivity, tripartite complexes produced with undesired targets in a first cell or tissue type are characterized by the presence of unfavorable interactions while the bifunctional molecule affects the desired target in a second cell or tissue type, e.g. a second type of cell or tissue in the same organism or a microorganism in a host organism, without formation of a binary complex between the bifunctional molecule and a presenter protein due to the lack of the presenter protein.

The subject methods and compositions find use in a variety of therapeutic applications.

DEFINITIONS

Figure 1A:
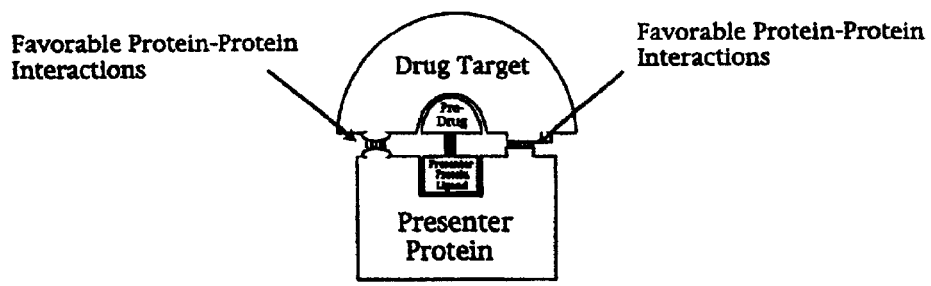
FIG. 1 provides an illustration of the general concept of the subject invention.

The term "affinity" refers to the nature of the binding of a first molecule to a second molecule, e.g. a drug moiety to its target, a presenter protein ligand to its presenter protein, etc. In other words, affinity is used to describe how strong a first molecule binds to a second molecule. The affinity of a bifunctional molecule of the subject invention to its target and its presenter protein can readily be determined by competitive binding assays or thermodynamic methods, as described in the experimental section infra.

The term "bifunctional molecule" refers to a non-naturally occurring molecule that includes a presenter protein ligand and a drug moiety, where these two components may be covalently bonded to each other either directly or through a linking group.

The term "binary complex" refers to a complex that is made up of a bifunctional molecule and its corresponding presenter protein, i.e. the complex that results from binding of the presenter protein ligand of the bifunctional molecule to the presenter protein.

The term "drug" refers to any active agent that affects any biological process.

Active agents which are considered drugs for purposes of this application are agents that exhibit a pharmacological activity. Examples of drugs include active agents that are used in the prevention, diagnosis, alleviation, treatment or cure of a disease condition.

By "pharmacologic activity" is meant an activity that modulates or alters a biological process so as to result in a phenotypic change, e.g. cell death, cell proliferation etc. The term "specificity" is used to describe the affinity profile of a drug with respect to its potential targets, i.e. it characterizes the differential affinity of a drug for its potential targets. The specificity of a drug can readily be ascertained by determining the affinity of a drug for each of its potential targets (i.e. how well the drug binds to each of its potential targets) and comparing the observed affinities to obtain an affinity profile of the drug. The term "selectivity" is used to characterize the activity profile of an active agent with respect to two or more different cell types. In other words, selectivity collectively describes the comparative activity of a drug in two or more different types of cells.

The term "tripartite complex" refers to a complex that is made up of a drug target, a bifunctional molecule and a presenter protein.

DESCRIPTION OF THE SPECIFIC EMBODIMENTS

Bifunctional molecules, synthesis and screening methods, and methods for their use in the production of at least binary complexes in a host are provided. The bifunctional molecules have a drug moiety covalently linked to a presenter protein ligand, either directly or through a linking group. In the subject methods, an effective amount of the bifunctional molecule is administered to the host. Upon administration, the bifunctional molecule binds to the presenter protein to produce the binary complex. The binary complex has an enlarged target binding surface area as compared to the free drug such that at least one of enhanced affinity, specificity or selectivity are observed as compared to the free drug. In a first embodiment in which increased affinity is observed, the binary complex binds to the target to form a tripartite complex characterized by the presence of presenter-target binding interactions as well as drug-target binding interactions. The subject methods and compositions find use in a variety of therapeutic applications. In further describing the subject invention, the bifunctional molecules and methods for their production will be described first, followed by a discussion of applications in which the bifunctional molecules find use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Though not wishing to be bound by any particular theory, the subject invention provides a means for improving at least one of the affinity or specificity or selectivity of a small molecule drug for its desired target by enlarging the target binding surface area of the drug moiety as compared to the free drug. Enhanced affinity, specificity or selectivity of the drug is accomplished by presenting it to its drug target as a binary complex made up of a bifunctional molecule of the drug and presenter protein ligand bound to a presenter protein. Interactions between the presenter protein and the drug target, such as favorable interactions, neutral interactions or repulsive interactions, in combination with interactions between the drug moiety and its target, result in a modulation of the overall binding profile of the drug moiety for its various targets, as compared to a free drug control. As such, by administering a small molecule drug as a bifunctional molecule according to the subject invention, one can achieve improved results as compared to the results obtainable by administration of the small molecule drug by itself. See FIG. 1.

Bifunctional Molecule

A critical element of the subject invention is the bifunctional molecule. The bifunctional molecule is a non-naturally occurring or synthetic compound. The bifunctional molecule is further characterized in that the presenter protein ligand and the drug moiety are different, such that the bifunctional molecule may be viewed as a heterodimeric compound produced by the joining of two different moieties. In many embodiments, the presenter protein ligand and the drug moiety are chosen such that the corresponding drug target and presenter protein do not naturally associate with each other to produce a biological effect. In many preferred embodiments, the bifunctional molecules are capable of simultaneously binding two distinct compounds, i.e. a target and a presenter protein, to form a tripartite complex. The bifunctional molecule has a drug moiety bonded to a ligand for a presenter protein, either directly or through a linking group. The molecular weight of the bifunctional molecule is generally at least about 100 D, usually at least about 400 D and more usually at least about 500 D, and may be as great as 2000 D or greater, but usually does not exceed about 5000 D.

The bifunctional molecule is further characterized in that the drug moiety has improved activity as compared to free drug. By improved activity is meant that the drug moiety has a more desirable effect with respect to the condition being treated, as compared to the corresponding free drug from which the drug moiety of the bifunctional molecule is derived. In many embodiments, the bifunctional molecule is characterized by having improved affinity for its target as compared to its corresponding drug, i.e. a control. The magnitude of enhanced affinity and/or specificity will be at least about 2 fold, usually at least about 5 fold and in many embodiments at least 10 fold. In many embodiments, the affinity of the bifunctional molecule for its target will be at least about $10^{-4}$ M, usually at least about $10^{-6}$ M. Additionally and/or alternatively, the bifunctional molecule exhibits improved specificity for its target as compared to a free drug control. Additionally and/or alternatively, the bifunctional molecule exhibits improved selectively for its target as compared to a free drug control.

Bifunctional molecules are generally described by the formula:

wherein X is a drug moiety;
L is bond or linking group; and
Z is a ligand for an endogenous presenter protein; with the proviso that X and Z are different.

Drug Moiety: X

The drug moiety X may be any molecule, as well as binding portion or fragment thereof, that is capable of modulating a biological process in a living host, either by itself or in the context of the presenter protein/bifunctional molecule binary complex. Generally, X is a small organic molecule that is capable of binding to the target of interest. As the drug moiety of the bifunctional molecule is a small molecule, it generally has a molecular weight of at least about 50 D, usually at least about 100 D, where the molecular weight may be as high as 500 D or higher, but will usually not exceed about 2000 D.

The drug moiety is capable of interacting with a target in the host into which the bifunctional molecule is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g. kinases, phosphatases, reductases, cyclooxygenases, proteases and the like, targets comprising domains involved in protein—protein interactions, such as the SH2, SH3, PTB and PDZ domains, structural proteins, e.g. actin, tubulin, etc., membrane receptors, immunoglobulins, e.g. IgE, cell adhesion receptors, such as integrins, etc, ion channels, transmembrane pumps, transcription factors, signaling proteins, and the like.

The drug moiety of the bifunctional compound will include one or more functional groups necessary for structural interaction with the target, e.g. groups necessary for hydrophobic, hydrophilic, electrostatic or even covalent interactions, depending on the particular drug and its intended target. Where the target is a protein, the drug moiety will include functional groups necessary for structural interaction with proteins, such as hydrogen bonding, hydrophobic—hydrophobic interactions, electrostatic interactions, etc., and will typically include at least an amine, amide, sulfhydryl, carbonyl, hydroxyl or carboxyl group, preferably at least two of the functional chemical groups. As described in greater detail below, the drug moiety will also comprise a region that may be modified and/or participate in covalent linkage to the other components of the bifunctional molecule, such as the presenter protein ligand or linker, without substantially adversely affecting the moiety's ability to bind to its target.

The drug moieties often comprise cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The drug moiety of the bifunctional molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the drug moiety may be obtained from a library of naturally occurring or synthetic molecules, including a library of compounds produced through combinatorial means, i.e. a compound diversity combinatorial library. When obtained from such libraries, the drug moiety employed will have demonstrated some desirable activity in an appropriate screening assay for the activity. Combinatorial libraries, as well as methods for the production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Specific drugs of interest from which the drug moiety may be derived include, but are not limited to: psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacinei derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives);

pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines ($H_1$-antagonists, $H_2$-antagonists), histamine metabolism drugs, (5) cardiovascular drugs, e.g. cardiotonics (plant extracts, butenolides, pentadienolids, alkaloids from erythropleum species, ionophores, -adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs;

chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like;

Antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; β-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, etc.; synthetic antibacterial agents, such as 2,4-diaminopyrimidines, nitrofurans, quinolones and analogs thereof, sulfonamides, sulfones;

Antifungal agents, such as: polyenes, e.g. amphotericin B, candicidin, dennostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

Anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Antiprotozoan agents, such as: acranil, tinidazole, ipronidazole, ethylstibamine,i pentamidine, acetarsone, aminitrozole, anisomycin, nifuratel, tinidazole, benzidazole, suramin, and the like.

Name brand drugs of interest include, but are not limited to: Rezulin™, Lovastatin™, Enalapril™, Prozac™, Prilosec™, Lipotor™, Claritin™, Zocor™, Ciprofloxacin™, Viagra™, Crixivan™, Ritalin™, and the like.

Drug compounds of interest from which drug moieties may be derived are also listed in: Goodman & Gilman's, The Pharmacological Basis of Therapeutics (9th Ed) (Goodman et al. eds) (McGraw-Hill) (1996); and 1999 Physician's Desk Reference (1998).

Specific compounds of interest also include, but are not limited to:

antineoplastic agents, as disclosed in U.S. Pat. Nos. 5,880,161, 5,877,206, 5,786,344, 5,760,041, 5,753, 668, 5,698,529, 5,684,004, 5,665,715, 5,654,484, 5,624,924, 5,618,813, 5,610,292, 5,597,831, 5,530, 026, 5,525,633, 5,525,606, 5,512,678, 5,508,277, 5,463,181, 5,409,893, 5,358,952, 5,318,965, 5,223, 503, 5,214,068, 5,196,424, 5,109,024, 5,106,996, 5,101,072, 5,077,404, 5,071,848, 5,066,493, 5,019, 390, 4,996,229, 4,996,206, 4,970,318, 4,968,800, 4,962,114, 4,927,828, 4,892,887, 4,889,859, 4,886, 790, 4,882,334, 4,882,333, 4,871,746, 4,863,955, 4,849,563, 4,845,216, 4,833,145, 4,824,955, 4,785, 085, 4,76,925, 4,684,747, 4,618,685, 4,611,066, 4,550, 187, 4,550,186, 4,544,501, 4,541,956, 4,532,327, 4,490,540, 4,399,283, 4,391,982, 4,383,994, 4,294, 763, 4,283,394, 4,246,411, 4,214,089, 4,150,231, 4,147,798, 4,056,673, 4,029,661, 4,012,448;

psycopharmacological/psychotropic agents, as disclosed in U.S. Pat. Nos. 5,192,799, 5,036,070, 4,778,800, 4,753,951, 4,590,180, 4,690,930, 4,645,773, 4,427, 694, 4,424,202, 4,440,781, 5,686,482, 5,478,828, 5,461,062, 5,387,593, 5,387,586, 5,256,664, 5,192, 799, 5,120,733, 5,036,070, 4,977,167, 4,904,663, 4,788,188, 4,778,800, 4,753,951, 4,690,930, 4,645, 773, 4,631,285, 4,617,314, 4,613,600, 4,590,180, 4,560,684, 4,548,938, 4,529,727, 4,459,306, 4,443, 451, 4,440,781, 4,427,694, 4,424,202, 4,397,853, 4,358,451, 4,324,787, 4,314,081, 4,313,896, 4,294, 828, 4,277,476, 4,267,328, 4,264,499, 4,231,930, 4,194,009, 4,188,388, 4,148,796, 4,128,717, 4,062, 858, 4,031,226, 4,020,072, 4,018,895, 4,018,779, 4,013,672, 3,994,898, 3,968,125, 3,939,152, 3,928, 356, 3,880,834, 3,668,210;

cardiovascular agents, as disclosed in U.S. Pat. No. 4,966, 967, 5,661,129, 5,552,411, 5,332,737, 5,389,675, 5,198,449, 5,079,247, 4,966,967, 4,874,760, 4,954, 526, 5,051,423, 4,888,335, 4,853,391, 4,906,634, 4,775,757, 4,727,072, 4,542,160, 4,522,949, 4,524, 151, 4,525,479, 4,474,804, 4,520,026, 4,520,026, 5,869,478, 5,859,239, 5,837,702, 5,807,889, 5,731, 322, 5,726,171, 5,723,457, 5,705,523, 5,696,111, 5,691,332, 5,679,672, 5,661,129, 5,654,294, 5,646, 276, 5,637,586, 5,631,251, 5,612,370, 5,612,323, 5,574,037, 5,563,170, 5,552,411, 5,552,397, 5,547, 966, 5,482,925, 5,457,118, 5,414,017, 5,414,013, 5,401,758, 5,393,771, 5,362,902, 5,332,737, 5,310, 731, 5,260,444, 5,223,516, 5,217,958, 5,208,245, 5,202,330, 5,198,449, 5,189,036, 5,185,362, 5,140, 031, 5,128,349, 5,116,861, 5,079,247, 5,070,099, 5,061,813, 5,055,466, 5,051,423, 5,036,065, 5,026, 712, 5,011,931, 5,006,542, 4,981,843, 4,977,144, 4,971,984, 4,966,967, 4,959,383, 4,954,526, 4,952, 692, 4,939,137, 4,906,634, 4,889,866, 4,888,335, 4,883,872, 4,883,811, 4,847,379, 4,835,157, 4,824, 831, 4,780,538, 4,775,757, 4,774,239, 4,771,047, 4,769,371, 4,767,756, 4,762,837, 4,753,946, 4,752, 616, 4,749,715, 4,738,978, 4,735,962, 4,734,426, 4,734,425, 4,734,424, 4,730,052, 4,727,072, 4,721, 796, 4,707,550, 4,704,382, 4,703,120, 4,681,970, 4,681,882, 4,670,560, 4,670,453, 4,668,787, 4,663, 337, 4,663,336, 4,661,506, 4,656,267, 4,656,185, 4,654,357, 4,654,356, 4,654,355, 4,654,335, 4,652, 578, 4,652,576, 4,650,874, 4,650,797, 4,649,139, 4,647,585, 4,647,573, 4,647,565, 4,647,561, 4,645, 836, 4,639,461, 4,638,012, 4,638,011, 4,632,931, 4,631,283, 4,628,095, 4,626,548, 4,614,825, 4,611, 007, 4,611,006, 4,611,005, 4,609,671, 4,608,386, 4,607,049, 4,607,048, 4,595,692, 4,593,042, 4,593, 029, 4,591,603, 4,588,743, 4,588,742, 4,588,741, 4,582,854, 4,575,512, 4,568,762, 4,560,698, 4,556, 739, 4,556,675, 4,555,571, 4,555,570, 4,555,523, 4,550,120, 4,542,160, 4,542,157, 4,542,156, 4,542, 155, 4,542,151, 4,537,981, 4,537,904, 4,536,514, 4,536,513, 4,533,673, 4,526,901, 4,526,900, 4,525, 479, 4,524,151, 4,522,949, 4,521,539, 4,520,026, 4,517,188, 4,482,562, 4,474,804, 4,474,803, 4,472, 411, 4,466,979, 4,463,015, 4,456,617, 4,456,616, 4,456,615, 4,418,076, 4,416,896, 4,252,815, 4,220, 594, 4,190,587, 4,177,280, 4,164,586, 4,151,297, 4,145,443, 4,143,054, 4,123,550, 4,083,968, 4,076, 834, 4,064,259, 4,064,258, 4,064,257, 4,058,620, 4,001,421, 3,993,639, 3,991,057, 3,982,010, 3,980, 652, 3,968,117, 3,959,296, 3,951,950, 3,933,834, 3,925,369, 3,923,818, 3,898,210, 3,897,442, 3,897, 441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927: 5,476,876, 5,472,973, 5,470,885, 5,470,842, 5,464,856, 5,464,849, 5,462,952, 5,459,151, 5,451,686, 5,444,043, 5,436,265, 5,432,181, RE034,918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 500,654, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219, 872, 5,219,873, 5,073,560, 5,073,560, 5,346,911, 5,424,301, 5,073,560, 5,219,872, 4,900,748, 4,786, 648, 4,798,841, 4,782,071, 4,710,508, 5,482,938, 5,464,842, 5,378,723, 5,346,911, 5,318,978, 5,219, 873, 5,219,872, 5,084,281, 5,073,560, 5,002,955, 4,988,710, 4,900,748, 4,798,841, 4,786,648, 4,782, 071, 4,745,123, 4,710,508;

adrenergic agents, as disclosed in U.S. Pat. Nos. 5,091, 528, 5,091,528, 4,835,157, 5,708,015, 5,594,027, 5,580,892, 5,576,332, 5,510,376, 5,482,961, 5,334, 601, 5,202,347, 5,135,926, 5,116,867, 5,091,528, 5,017,618, 4,835,157, 4,829,086, 4,579,867, 4,568, 679, 4,469,690, 4,395,559, 4,381,309, 4,363,808, 4,343,800, 4,329,289, 4,314,943, 4,311,708, 4,304, 721, 4,296,117, 4,285,873, 4,281,189, 4,278,608, 4,247,710, 4,145,550, 4,145,425, 4,139,535, 4,082, 843, 4,011,321, 4,001,421, 3,982,010, 3,940,407, 3,852,468, 3,832,470;

antihistamine agents, as disclosed in U.S. Pat. Nos. 5,874, 479, 5,863,938, 5,856,364, 5,770,612, 5,702,688, 5,674,912, 5,663,208, 5,658,957, 5,652,274, 5,648, 380, 5,646,190, 5,641,814, 5,633,285, 5,614,561, 5,602,183, 4,923,892, 4,782,058, 4,393,210, 4,180, 583, 3,965,257, 3,946,022, 3,931,197;

steroidal agents, as disclosed in U.S. Pat. Nos. 5,863,538, 5,855,907, 5,855,866, 5,780,592, 5,776,427, 5,651, 987, 5,346,887, 5,256,408, 5,252,319, 5,209,926, 4,996,335, 4,927,807, 4,910,192, 4,710,495, 4,049, 805, 4,004,005, 3,670,079, 3,608,076, 5,892,028, 5,888,995, 5,883,087, 5,880,115, 5,869,475, 5,866, 558, 5,861,390, 5,861,388, 5,854,235, 5,837,698, 5,834,452, 5,830,886, 5,792,758, 5,792,757, 5,763, 361, 5,744,462, 5,741,787, 5,741,786, 5,733,899, 5,731,345, 5,723,638, 5,721,226, 5,712,264, 5,712, 263, 5,710,144, 5,707,984, 5,705,494, 5,700,793, 5,698,720, 5,698,545, 5,696,106, 5,677,293, 5,674, 861, 5,661,141, 5,656,621, 5,646,136, 5,637,691, 5,616,574, 5,614,514, 5,604,215, 5,604,213, 5,599, 807, 5,585,482, 5,565,588, 5,563,259, 5,563,131, 5,561,124, 5,556,845, 5,547,949, 5,536,714, 5,527, 806, 5,506,354, 5,506,221, 5,494,907, 5,491,136, 5,478,956, 5,426,179, 5,422,262, 5,391,776, 5,382, 661, 5,380,841, 5,380,840, 5,380,839, 5,373,095, 5,371,078, 5,352,809, 5,344,827, 5,344,826, 5,338, 837, 5,336,686, 5,292,906, 5,292,878, 5,281,587, 5,272,140, 5,244,886, 5,236,912, 5,232,915, 5,219, 879, 5,218,109, 5,215,972, 5,212,166, 5,206,415, 5,194,602, 5,166,201, 5,166,055, 5,126,488, 5,116, 829, 5,108,996, 5,099,037, 5,096,892, 5,093,502, 5,086,047, 5,084,450, 5,082,835, 5,081,114, 5,053, 404, 5,041,433, 5,041,432, 5,034,548, 5,032,586, 5,026,882, 4,996,335, 4,975,537, 4,970,205, 4,954, 446, 4,950,428, 4,946,834, 4,937,237, 4,921,846, 4,920,099, 4,910,226, 4,900,725, 4,892,867, 4,888, 336, 4,885,280, 4,882,322, 4,882,319, 4,882,315, 4,874,855, 4,868,167, 4,865,767, 4,861,875, 4,861, 765, 4,861,763, 4,847,014, 4,774,236, 4,753,932, 4,711,856, 4,710,495, 4,701,450, 4,701,449, 4,689, 410, 4,680,290, 4,670,551, 4,664,850, 4,659,516, 4,647,410, 4,634,695, 4,634,693, 4,588,530, 4,567, 000, 4,560,557, 4,558,041, 4,552,871, 4,552,868, 4,541,956, 4,519,946, 4,515,787, 4,512,986, 4,502, 989, 4,495,102;

the disclosures of which are herein incorporated by reference.

The drug moiety of the bifunctional molecule may be the whole compound or a binding fragment or portion thereof that retains its affinity and specificity for the target of interest while having a linkage site for covalent bonding to the presenter protein ligand or linker.

Presenter Protein Ligand: Z

Z is a ligand for a presenter protein present in the host into which the bifunctional molecule is to be administered. The presenter protein ligand of the subject bifunctional molecules binds to a specific presenter protein present in the host. The binding interaction between the presenter protein and the presenter protein ligand is non-covalent, such that no covalent bonds are produced between the bifunctional molecule and the presenter protein upon binding of the two entities. The presenter protein ligand is small, where the size of the presenter protein ligand does not exceed about 4950 daltons, usually does not exceed about 4925 daltons and more usually does not exceed about 4900 daltons, where the size of the presenter protein ligand is generally at least about 50 daltons and more usually at least about 100 daltons. The presenter protein ligand, in the context of the bifunctional molecule, has substantially no pharmacological activity at its effective concentration beyond binding to the presenter protein, i.e. it does not directly cause a presenter protein-mediated pharmacological event to occur upon binding at its effective concentration to the presenter protein, where a presenter protein-mediated pharmacological event is a pharmacologically relevant event which is directly modulated by the presenter protein in the absence of the subject bifunctional molecules. As used herein, pharmacological event is an event that is distinct from a biochemical event (e.g. inhibition a prolyl isomerase activity) or a biological event (e.g. inducement of a cell to express new genes).

The presenter protein to which the ligand of the bifunctional molecule binds may be any protein that is present in the host at the time the bifunctional molecule is introduced to the host, i.e. the presenter protein will be endogenous to the host. The presenter protein may or may not have one or more modified residues, e.g. residues that are glycosylated, such that the presenter protein may or may not be a glycoprotein. Furthermore, the presenter protein that is recruited by the bifunctional molecule may or may not be part of a complex or structure of a plurality of biological molecules, e.g. lipids, where such complexes or structures may include lipoproteins, lipid bilayers, and the like. However, in many embodiments, the presenter protein that is recruited by the presenter protein ligand of the bifunctional molecule will be by itself, i.e. will not be part of a larger structure of a plurality of biological molecules. Though the presenter protein may be a protein that is not native to the host but has been introduced at some time prior to introduction of the bifunctional molecule, e.g. through prior administration of the protein or a nucleic acid composition encoding the same, such as through gene therapy, the presenter protein will, in many embodiments, be a protein that is native to and naturally expressed by at least some of the host's cells, i.e. a naturally occurring protein in the host. The presenter protein is a protein that is present in the region of host occupied by the drug target. As such, where the drug target is an intracellular drug target, the presenter protein will be an intracellular protein present in the cell comprising the target, typically expressed in the cell comprising the target, i.e. the presenter protein and target are co-expressed in the same cell. Likewise, where the drug target is an extracellular drug target, the presenter protein will be an extracellular protein that is found in the vicinity of the target.

Although not a requirement in certain embodiments, in many preferred embodiments the presenter protein is one that is present in the host in sufficient quantities such that, upon binding of at least a portion of presenter protein present in the host to the bifunctional molecule, adverse pharmacological effects do not occur. In other words, the presenter protein in these preferred embodiments is one in which its native and desirable biological activity, if any, is not diminished by an unacceptable amount following binding of the portion of the presenter protein population to the bifunctional molecule. The amount of diminished activity of the presenter protein that is acceptable in a given situation is determined with respect to the condition being treated in view of the benefits of treatment versus the reduction of overall presenter protein activity, if any. In certain situations, a large decrease in overall presenter protein activity may be acceptable, e.g. where the presenter protein activity aggravates the condition being treated.

Specific presenter proteins of interest include intracellular and extracellular proteins. Intracellular proteins of interest include: peptidyl-prolyl isomerases, e.g. FKBPs and cyclophilins; ubiquitously expressed molecular chaperones, e.g. Heat Shock Protein 90 (Hsp90); steroid hormone receptors, e.g. estrogen receptors, glucocorticoid receptors, androgen receptors; retinoic acid binding protein, cytoskeletal proteins, such as tubulin and actin; etc.

Of particular interest as intracellular presenter proteins are cis-trans peptidyl-prolyl isomerases which interact with many proteins because of their chaperonin/isomerase activity, e.g. FKBPs and cyclophilins. Peptidyl-prolyl isomerases of interest include FKBPs. A number of different FKBPs are known in the art, and include those described in: Sabatini et al., Mol. Neurobiol. (Oct. 1997) 15:223–239; Marks, Physiol. Rev. (July 1996) 76:631–649; Kay, Biochem J. (March, 1996) 314: 361–385; Braun et al., FASEB J. (January 1995) 9:63–72; Fruman et al, FASEB J. (April 1994) 8:391–400; and Hacker et al., Mol. Microbiol. (November 1993) 10: 445–456. FKBPs of interest include FKBP 12, FKBP 52, FKBP 14.6 (described in U.S. Pat. No. 5,525,523, the disclosure of which is herein incorporated by reference); FKBP 12.6 (described in U.S. Pat. No. 5,457,182 the disclosure of which is herein incorporated by reference); FKBP 13 (described in U.S. Pat. No. 5,498,597, the disclosure of which is herein incorporated by reference); and HCB (described in U.S. Pat. No. 5,196,352 the disclosure of which is herein incorporated by reference); where FKBP 12 and FKBP 52 are of particular interest as intracellular presenter proteins.

Also of specific interest as presenter proteins are cyclophilins. A number of cyclophilins are known in the art and are described in Trandinh et al., FASEB J. (December 1992) 6: 3410–3420; Harding et al., Transplantation (August 1988) 46: 29S-35S. Specific cyclophilins of interest as intracellular presenter proteins include cyclophilin A, B, C, D, E, and the like, where cyclophilin A is of particular interest.

Instead of being an intracellular protein, the endogenous presenter protein may be an extracellular or serum protein. Serum presenter proteins of particular interest are those that are relatively abundant in the serum of the host and meet the above criteria for suitable endogenous presenter proteins. By relatively abundant is meant that the concentration of the serum presenter protein is at least about 1 ng/ml, usually at least about 10 g/ml and more usually at least about 15 g/ml. Specific serum proteins of interest as presenter proteins include: albumin, Vitamin A binding proteins and Vitamin D binding proteins, -2 macroglobulin, with albumin being a particularly preferred presenter protein.

The Z moiety of the subject bifunctional molecules will therefore be chosen in view of the endogenous presenter protein that is to be recruited to produce the at least binary and, in some embodiments, tripartite complex. As such, the Z moiety may be a number of different ligands, depending on the particular endogenous presenter protein to which it is intended to bind. In many preferred embodiments, the Z moiety has an affinity for its presenter protein of at least about $10^{-4}$ M, usually at least about $10^{-6}$ molar and more usually at least about $10^{-8}$ M, where in many embodiments the Z moiety has an affinity for its presenter protein of between about $10^{-9}$ and $10^{-12}$ M. The Z moiety portion of the bifunctional molecule should also be specific for the presenter protein in the context of its binding activity when present in the bifunctional molecule, in that it does not significantly bind or substantially affect non-presenter proteins when it is present in the bifunctional molecule.

Representative ligands capable of serving as the Z moiety of the bifunctional molecule include ligands for intracellular proteins, such as: peptidyl-prolyl isomerase ligands, e.g. FK506, rapamycin, cyclosporin A and the like; Hsp90 ligands, e.g. geldanamycin; steroid hormone receptor ligands, e.g. naturally occurring steroid hormones, such as estrogen, progestin, testosterone, and the like, as well as synthetic derivatives and mimetics thereof, particularly those which bind with high specificity and affinity but do not activate their respective receptors; small molecules that bind to cytoskeletal proteins, e.g. antimitotic agents, such as taxanes, colchicine, colcemid, nocadozole, vinblastine, and vincristine, actin binding agents, such as cytochalasin, latrunculin, phalloidin, and the like.

As mentioned above, the preferred intracellular presenter proteins are members of the peptidyl-prolyl isomerase family, particularly the FKBP and cyclophilin subsets of this family. Where peptidyl-prolyl isomerase presenter proteins are employed, the bifunctional molecule/peptidyl-prolyl isomerase complex will preferably not substantially bind to the natural peptidyl-prolyl isomerase/ligand target calcineurin so as to result in significant immunosuppression. A variety of ligands are known that bind to FKBPs and may be used in the subject invention. The ligands should specifically bind to an FKBP and have an affinity for the FKBP that is between about $10^{-6}$ and $10^{-10}$ M. Of interest are both naturally occurring FKBP ligands, including FK506 and rapamycin. Also of interest are synthetic FKBP ligands, including those described in U.S. Pat. Nos. 5,665,774; 5,622,970; 5,516,797; 5,614,547; and 5,403,833, the disclosures of which are herein incorporated by reference.

Also of interest are cyclophilin ligands, where such ligands should specifically bind to cyclophilin with an affinity that is between about $10^{-6}$ and $10^{-9}$ M. A variety of ligands that bind to cyclophilins are also known, where such ligands include the naturally occurring cyclosporins, such as cyclosporin A, as well as synthetic derivatives and mimetics thereof, including those described in U.S. Pat. Nos. 5,401, 649; 5,318,901; 5,236,899; 5,227,467; 5,214,130; 5,122, 511; 5,116,816; 5,089,390; 5,079,341; 5,017,597; 4,940, 719; 4,914,188; 4,885,276; 4,798,823; 4,771,122; 4,703, 033; 4,554,351; 4,396,542; 4,289,851; 4,288,431; 4,220,61 and 4,210,581, the disclosures of which are herein incorporated by reference.

Representative ligands for use as the Z moiety in the bifunctional molecule also include ligands that bind to extracellular presenter proteins. Such ligands should specifically bind to their respective presenter protein with an affinity of at least about $10^{-4}$ M. Ligands of interest for use in binding to extracellular presenter proteins include: albumin ligands, such as arachidonate, bilirubin, hemin, aspirin, ibuprofen, para-amino salicylic acid, myristylate, plamitate, linoleate, warfarin etc.; Vitamin A and derivatives thereof, Vitamin D and derivatives thereof, and the like.

Linking Moiety: L

The Z and X moieties of the bifunctional molecule are joined together through linking moiety L, where L may be either a bond or a linking group. Where linking groups are employed, such groups are chosen to provide for covalent attachment of the drug and ligand moieties through the linking group, as well as the desired structural relationship of the bifunctional molecule with respect to its intended presenter protein. Linking groups of interest may vary widely depending on the nature of the drug and ligand moieties. The linking group, when present, should preferably be biologically inert. Appropriate linkers can readily be identified using the affinity, specificity or selectivity assays described supra. A variety of linking groups are known to those of skill in the art and find use in the subject bifunctional molecules. The linker groups should be sufficiently small so as to provide a bifunctional molecule having the overall size characteristics as described above, the size of the linker group, when present, is generally at least about 50 daltons, usually at least about 100 daltons and may be as large as 1000 daltons or larger, but generally will not exceed about 500 daltons and usually will not exceed about 300 daltons. Generally, such linkers will comprise a spacer group terminated at either end with a reactive functionality capable of covalently bonding to the drug or ligand moieties. Spacer groups of interest possibly include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject bifunctional molecules include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl 4-[N-maleimidomethyl] cyclohexane-l-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

Methods of Making Bifunctional Molecules

The bifunctional molecules of the subject invention may be prepared using any convenient methodology. In many embodiments of the subject invention, the invention is used to improve one or more aspects of an identified and at least partially characterized small molecule drug. Generally, a small molecule drug of interest but lacking in some of the desired biological activities, such as affinity, specificity or selectivity, is first identified. The drug may be a previously identified biologically active agent or compound having the desired target binding activity, or one that has been newly discovered using one or more drug discovery techniques. The bifunctional molecule is then generally produced from the drug using a rational or combinatorial approach.

In a rational approach, the bifunctional molecules are constructed from their individual components, e.g. ligand, linker and drug. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the bifunctional molecule include: hydroxy, sulfhydryl, amino, and the like. The particular portion of the different components that are modified to provide for covalent linkage will be chosen so as not to substantially adversely interfere with that components desired binding activity, e.g. for the drug moiety, a region that does not affect the target binding activity will be modified, such that a sufficient amount of the desired drug activity is preserved. Where necessary and/or desired, certain moieties on the components may be protected using blocking groups, as is known in the art, see, e.g. Green & Wuts, Protective Groups in Organic Synthesis (John Wiley & Sons) (1991).

The above component approach to production of the bifunctional molecule is best suited for situations where the crystal structures of the presenter protein, ligand, drug and target are known, such that molecular modeling can be used to determine the optimal linker size, if any, to be employed to join the different components.

Alternatively, the bifunctional molecule can be produced using combinatorial methods to produce large libraries of potential bifunctional molecules which may then be screened for identification of a bifunctional molecule with the desired binding affinity and/or specificity. Methods for producing and screening combinatorial libraries of molecules include: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Alternatively, the bifunctional molecule may be produced using medicinal chemistry and known structure-activity relationships for the presenter protein ligand and the drug. In particular, this approach will provide insight as to where to join the two moieties to the linker.

Screening Bifunctional Compounds

The resultant bifunctional molecules are then screened for those molecules that exhibit at least one of enhanced affinity, specificity or selectivity as compared to that observed for the free drug. Any convenient screening assay may be employed, where the particular screening assay may be one known to those of skill in the art or one developed in view of the specific molecule and property being studied. Typically, the screening assay will involve observing the binding activity of the bifunctional molecule to the target in the presence of an appropriate presenter protein. For example, where one is interested in identifying those bifunctional molecules that exhibit enhanced affinity for their targets as compared to the free drug, one can conduct binding assays and select those bifunctional molecules that exhibit enhanced affinity, where the affinity will generally be at least about 2 fold greater than that observed for the free drug, as described above. For specificity, an assay can be used that focuses on the binding of the bifunctional molecule to both desirable and undesirable targets. For example, where one is interested in identifying those bifunctional molecules that exhibit improved specificity as compared to the corresponding free drug, where the free drug binds to both desirable target A and undesirable target B, one can screen the library for those bifunctional molecules that, in the presence of presenter protein, bind to target A but with reduced amounts, if at all, to target B, as such bifunctional molecules are more specific for the desired target than free drug. For selectivity, an assay can be used to compare the activity of a bifunctional molecule in the target cell or tissue type to the activity of the bifunctional molecule in cells or tissues in which drug activity is not desired. A selective bifunctional molecule will affect the target in the desired cells, e.g. cells involved in a disease process, but it will not affect (or at least affect to a lesser extent) the target in undesired cells, e.g. cells not involved in the disease process.

For example, a prospective drug may bind to target A in both the host and a pathogenic microorganism. By adding a ligand for a presenter protein to the drug, target A in the host is unable to bind the drug due to interactions with the presenter protein, while the drug retains its potency in the microorganism.

Methods of Making Bifunctional Molecules for Peptidyl-Prolyl Isomerase Presenter Proteins As mentioned above, one class of preferred embodiments of the subject invention are those embodiments in which the bifunctional molecules specifically bind to endogenous peptidyl-prolyl isomerase presenter proteins present in the host into which the bifunctional molecule is introduced. Thus, bifunctional molecules of interest include those in which the endogenous presenter protein is either an FKBP or a cyclophilin.

In preparing bifunctional molecules from FK506, a suitable attachment site on the FK506 structure is identified, modified as necessary, and then covalently attached to the linker or drug moiety. The structure of FK506 (also known as tacrolimus) is:

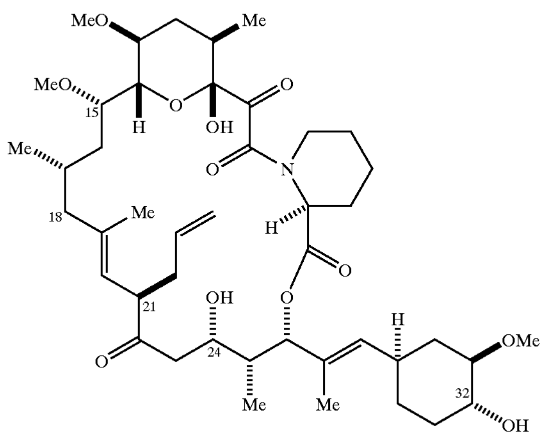

The site to which the linker/drug moiety is covalently attached is one that, upon covalent attachment, does not ablate the affinity and/or specificity of FK506 for its FKBP presenter protein, e.g. FKBP 12 or FKBP 52.As such, positions suitable for use as covalent linkage sites include atoms located between carbon 15 and carbon 25 and the substituents attached to these atoms. For example, oxidation of the allyl group or oxidation of the carbon 18 methylene group; modification of the carbon 22 ketone or the carbon 24 hydroxyl group or alkylation at carbon 21 or carbon 23; as well as the secondary hydroxyl group located on the cyclohexyl ring (carbon 32); are potential specific covalent linkage sites.

With FK506, depending on the drug moiety and/or linker to be attached, it may be desirable to introduce one or more functional moieties onto the FK506 structure. Functional moieties of interest that may be introduced include: hydroxyl groups, amino groups, carboxyl groups, aldehydes, carbonates, carbamates, azides, thiols, and esters, etc. Such groups may be introduced using known protocols, such as oxidation reactions, reduction reactions, cleavage reactions and the like, with or without the use of one or more blocking groups to prevent unwanted side reactions.

In some instances, it is desirable to covalently attach the drug moiety directly to FK506, often activated FK506. In such instances, the reactive functional group(s) introduced onto the FK506 structure will depend primarily on the nature of the drug moiety to be attached. Thus, for peptidic drug moieties, specific pairings of interest include: FK506 carbonates for reacting with amino groups of peptides; FK506 carboxylic acids for reacting with amino groups of peptides; FK506 amines for reacting with carboxylic acid groups of peptides; FK506 maleimide for reacting with thiol groups of peptides; and the like. Alternatively, where the drug moiety is a steroid, potential pairings of interest include: FK506 N-hydroxysuccinimidyl carbonate and partner amine; FK506 aldehyde and partner amine; FK506 aldehyde and partner hydrazide; FK506 hydroxy group and partner carboxylic acid OR alkyl halide; FK506 thiol and partner maleimide and the like.

Following introduction of the reactive functional group(s) onto the FK506 structure, the activated FK506 is then combined with the drug moiety/linker under conditions sufficient for covalent bonding to occur.

Another embodiment of particular interest are bifunctional molecules of cyclosporin A or analogs thereof. The structure of cyclosporin A is:

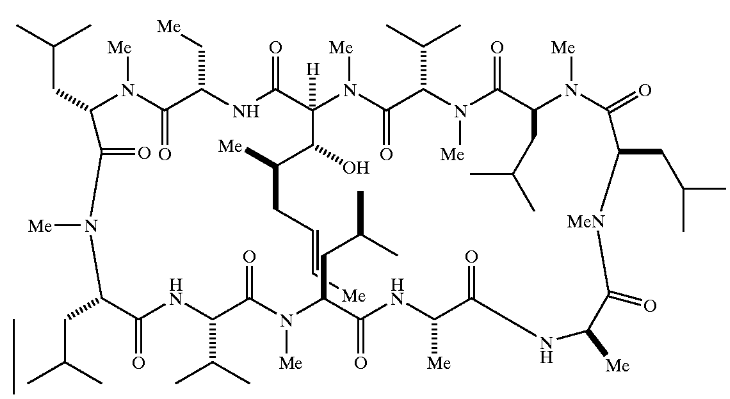

As with the FK506 bifunctional molecules, the cyclosporin A will be conjugated to the drug moiety in a manner such that cyclosporin A does not substantially lose its affinity for cyclophilin. Preferred positions on the cyclosporin A structure that may serve as covalent linkage sites include: residues 4, 5, 6, 7, 8; while less preferred but still possible residues include: 1, 2, 3, 9, 10 and 11. Where necessary, reactive functionalities may be introduced onto the cyclosporin structure, where such functionalities include: hydroxyl groups, amino groups, carboxyl groups, aldehydes, carbonates, carbamates, azides, thiols, and esters, etc., with the particular functionality of interest being chosen with respect to the specific linker or drug moiety to be attached.

Specific Improvements as Compared to Free Drug

As mentioned above, the bifunctional molecules of the subject invention provide for specific improvements over the overall activity observed in the corresponding free drug, i.e. the bifunctional molecules exhibit at least one of enhanced affinity, specificity or selectivity as compared to free drug, i.e. a free drug control. Though not wishing to be bound to any particular theory, the improved activity as compared to free drug is thought to result from the enlarged target binding surface present on the binary complex or optimization of favorable interactions as compared to that found on the free drug. In other words, presentation of the drug as a binary complex of the bifunctional molecule and its presenter protein modulates the overall binding profile of the drug moiety with respect to its targets in a way that improves at least one of the affinity, specificity or selectivity of the drug as compared to a free drug control. This modulation of binding profile can result from the combination of drug-target interactions and presenter protein-drug target interactions, where the presenter protein-drug target interactions may be attractive, repulsive or neutral. See FIG. 1.

Figure 1B:
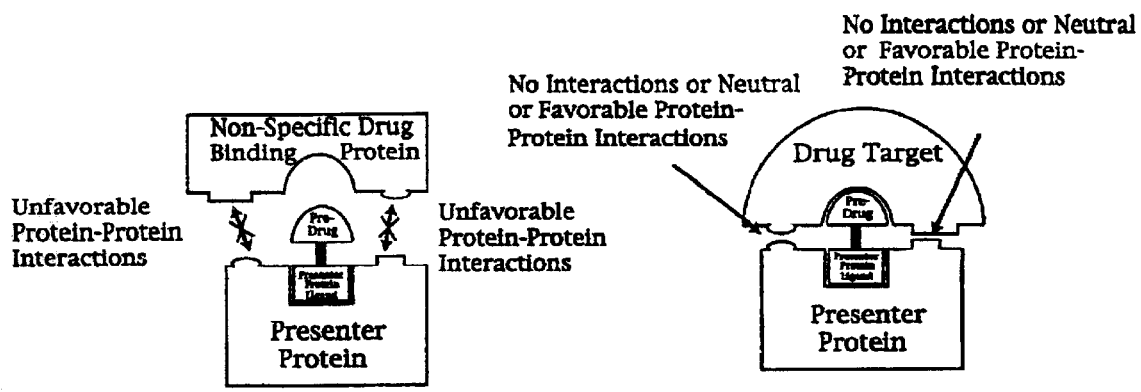
Figure 1C:
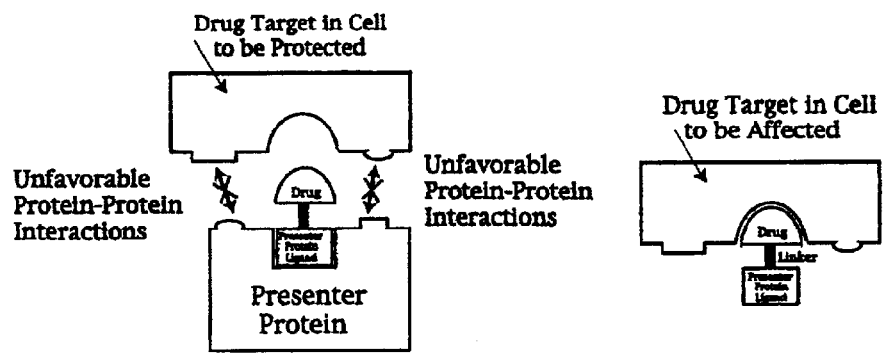

FIG. 1A provides a representation of how enhanced affinity is achieved with the subject invention. As shown, the drug target establishes favorable or attractive protein—protein interactions with a presenter protein that presents the drug moiety of the bifunctional compound. These favorable interactions between the presenter protein and the drug target enhance the affinity of the drug for its target. FIG. 1B provides a representation of how enhanced specificity is achieved with the subject bifunctional compounds. In FIG. 1B, a non-specific drug binding protein (i.e. an undesirable target) cannot bind the drug moiety in the context of the presenter protein because of unfavorable protein—protein interactions between the presenter protein and the non-specific drug binding protein. As such, enhanced specificity is observed since the drug can only bind to its bona fide drug target. FIG. 1C provides a representation of how enhanced selectivity is achieved with the subject bifunctional compounds, where activity of the drug is limited to one type of cell or another within an organism.

Thus, in a first preferred embodiment, the bifunctional molecule provides for enhanced or greater affinity for the target as compared to the free drug. In preferred embodiments of the subject invention, the enhanced affinity results from positive, i.e. attractive, interactions between the presenter and target as well as between the drug and target. As such, improved affinity results from the production of a tripartite complex characterized by the presence of both drug/target binding interactions and presenter/target binding interactions.

In a second preferred embodiment of the subject invention, the bifunctional molecule provides enhanced specificity as compared to the free drug. In such situations, the bifunctional molecule/presenter protein binary complex exhibits negative or repulsive interactions with at least some, if not all, of the free drug's targets but not for the desired target, where any repulsive or negative interactions arising from the presentation of the drug moiety in the context of the presenter protein are insufficient to prevent a suitable amount of binding of drug to the desired target. Thus, tripartite complexes produced between the binary complex and undesired targets are, in at least some cases, characterized by the presence of negative or repulsive interactions. Administration of the drug as a bifunctional molecule according to the subject invention provides for the desired activity, without the undesirable activity that arises from the low specificity of the free drug.

In a third embodiment of the subject invention, the bifunctional molecule provides for enhanced selectivity as compared to the free drug. In this embodiment, the bifunctional molecule exhibits activity in a first type of cell but not in a second type of cell. This selective activity is based on the formation of a binary complex between the bifunctional molecule and a presenter protein ligand that is present in a first type of cell but not in a second type of cell. Depending on the particular bifunctional molecule and drug target, the drug moiety may only exhibit activity when presented to the target in the form of a binary complex with the presenter protein. Conversely, the drug moiety may exhibit activity only when presented to the drug target as the bifunctional molecule by itself.

As such, in certain embodiments, the bifunctional molecule is engineered to have a presenter protein ligand that binds to a presenter protein present only in those cells that harbor the desired drug target, where activity of the drug moiety is at least enhanced when it is presented to the drug target by the presenter protein. Those cells which harbor the undesired target also lack the presenter protein. As such, the drug moiety of the bifunctional molecule exhibits less activity in these cells since it is not presented by a presenter protein to the drug target. In this manner, the activity of the drug moiety has been selectively enhanced in the first type of cell that comprises the desired drug target and presenter protein as compared to the second type of cell that harbors the undesired drug target and lacks the presenter protein.

In other embodiments, the drug of interest is one that binds in its free drug state to a desired target in a first type of cell but also to an undesired target in a second type of cell. Examples of such drugs include antimicrobial agents, such as antibiotics, which bind to desirable targets in microorganisms but undesirable targets in other types of cells, such as host cells in which the microorganism is present. In this embodiment, the bifunctional molecule is one that comprises a ligand for a presenter protein that is present in those cells comprising the undesirable target(s) but is not present in those cells harboring the desired target. In other words, the presenter ligand Z of the bifunctional molecule may be any ligand that binds to a protein present in those cells comprising the undesirable target but not present in those cells that have the desired target. The particular presenter ligand that is employed will necessarily depend on the nature of the two types of cells among which differentiation in drug activity is desired. For example, where the two types of cells are microbial and human cells, the presenter protein ligand may be one that binds to a protein that is present in the human cells but not present in the microbial cells, e.g. FKBPs, and the like. The bifunctional molecule/presenter protein binary complex is unable to bind to the undesirable targets in those cells that do not comprise the desired target. At the same time, the free bifunctional molecule is able to bind to the desired target in those cells that comprise the desired target because of repulsive interactions between the binary complex and the undesirable target. For example, where the drug moiety is a particular antibiotic that exhibits desired activity in bacterial cells but undesirable activity in human cells, the bifunctional molecule is able to bind to the bacterial target but the bifunctional molecule/binary complex is not able to bind to the human target(s). See FIG. 1C. As such, the bifunctional molecule provides for enhanced selectivity as compared to the free drug.

Preferred drugs in this third embodiment are molecules which exhibit considerable side effects and toxicity in human cells in addition to a desired activity in target cells. Many of these molecules target metabolic pathways and biological activities that are common to the target cell as well as non-target cells, such as: inhibitors of RNA polymerase II like -aminitin, rifamycin, rifampicin and actinomycin D; protein synthesis inhibitors like cycloheximide, streptomycin, tetracycline, chloramphenicol, erythromycin or puromycin; dihydrofolate reductase inhibitiors like methotrexate; topoisomerase II inhibitors like novobiocin and ciprofloxacin, proteasome inhibitors like lactacystin; channel inhibitors.

This embodiment finds particular use in the targeting of a drug to a microbial pathogen while reducing toxicity to the host in which the microbial pathogen is present. Microbial pathogens that may be targeted include Legionella sp., Chlamydia sp., Staphylococcus sp., Neisseria sp., Rickettsia sp., Coxiella sp., Neurospora sp., *Escherischia coli, Heliobacter pylori* as well as protozoan pathogens like Plasmodium sp., Leishmania sp., Trypanosoma sp., *Entamoeba histolytica, Giardia lamblia, Trichomonas vaginalis.*

In one particular embodiment of interest, the drug is selected from the group consisting of methotrexate and puromycin which are linked to a presenter ligand such that DHFR and protein synthesis, respectively, are less affected in cells containing the presenter protein (e.g. FKBP), e.g. host cells, than in cells that lack the presenter, e.g. pathogen cells.

Methods of use, Pharmaceutical Preparations and Kits

The subject bifunctional molecules find use in producing at least binary complexes in vivo, where the production of these complexes is desirous to the host in which they occur, e.g. is beneficial to the host. The term binary complex is used throughout this specification to refer to any complex produced by the non-covalent binding of two distinct molecules, i.e. the bifunctional molecule and the presenter protein or the bifunctional molecule and the protein target. In many preferred embodiments, tripartite complexes are produced with the subject bifunctional molecules. The term tripartite complex is used throughout this specification to refer to binding complexes of three distinct entities, i.e. the protein drug target, the bifunctional molecule and the presenter protein.

In the methods of the subject invention, an effective amount of the bifunctional molecule is administered to the host, where "effective amount" means a dosage sufficient to produce the desired result, e.g. an improvement in a disease condition or the symptoms associated therewith. The bifunctional molecule may be administered to the host using any convenient means capable of producing the desired result. Thus, the bifunctional molecule can be incorporated into a variety of formulations for therapeutic administration. More particularly, the bifunctional molecule of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the bifunctional molecule can be achieved in various ways, including oral, buccal, rectal, parenteral, intraperitoneal, intradermal, transdermal, intracheal, etc., administration. In pharmaceutical dosage forms, the bifunctional molecule may be administered alone or in combination with other pharmaceutically active compounds. The following methods and excipients are merely exemplary and are in no way limiting.

For oral preparations, the bifunctional molecules can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The bifunctional molecules can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The bifunctional molecules can be utilized in aerosol formulation to be administered via inhalation. The compounds of the present invention can be formulated into pressurized acceptable propellants such as dichlorodifluoromethane, propane, nitrogen and the like.

Furthermore, the bifunctional molecules can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions. In certain embodiments, of particular interest is the use of the subject methods in disease conditions where an active agent or drug having desired activity has been previously identified, but which active agent or drug does not bind to its target with desired affinity and/or specificity. With such active agents or drugs, the subject methods can be used to enhance the binding affinity and/or specificity of the agent for its target.

The specific disease conditions treatable by with the subject bifunctional compounds are as varied as the types of drug moieties that can be present in the bifunctional molecule. Thus, disease conditions include cellular proliferative diseases, such as neoplastic diseases, autoimmune diseases, cardiovascular diseases, hormonal abnormality diseases, infectious diseases, and the like.

By treatment is meant at least an amelioration of the symptoms associated with the disease condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the bifunctional molecule, usually in oral or injectable doses and often in a storage stable formulation, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

EXPERIMENTAL

EXAMPLE I

Bifunctional Molecules of pYEEI

SH2 domains of the tyrosine kinases Fyn and Lck as well as the N-terminal SH2 domain of PLC were used to demonstrate that the affinity and specificity of a ligand that is bound by multiple proteins can be improved through the use of presenter proteins. While Fyn, Lck and PLCy have similar biochemical properties, they are involved in different signaling processes affecting different biological endpoints. The ligand studied was a phosphotyrosine peptide with the sequence $NH_2$-pYEEI-COOH. This peptide binds to all three SH2 domains, Fyn, Lck and PLC [Songyang et al. Cell (1993) 72, 767].

A. Bifunctional Molecule Synthesis

1. Synthesis of FKpYEEI

Figure 2:
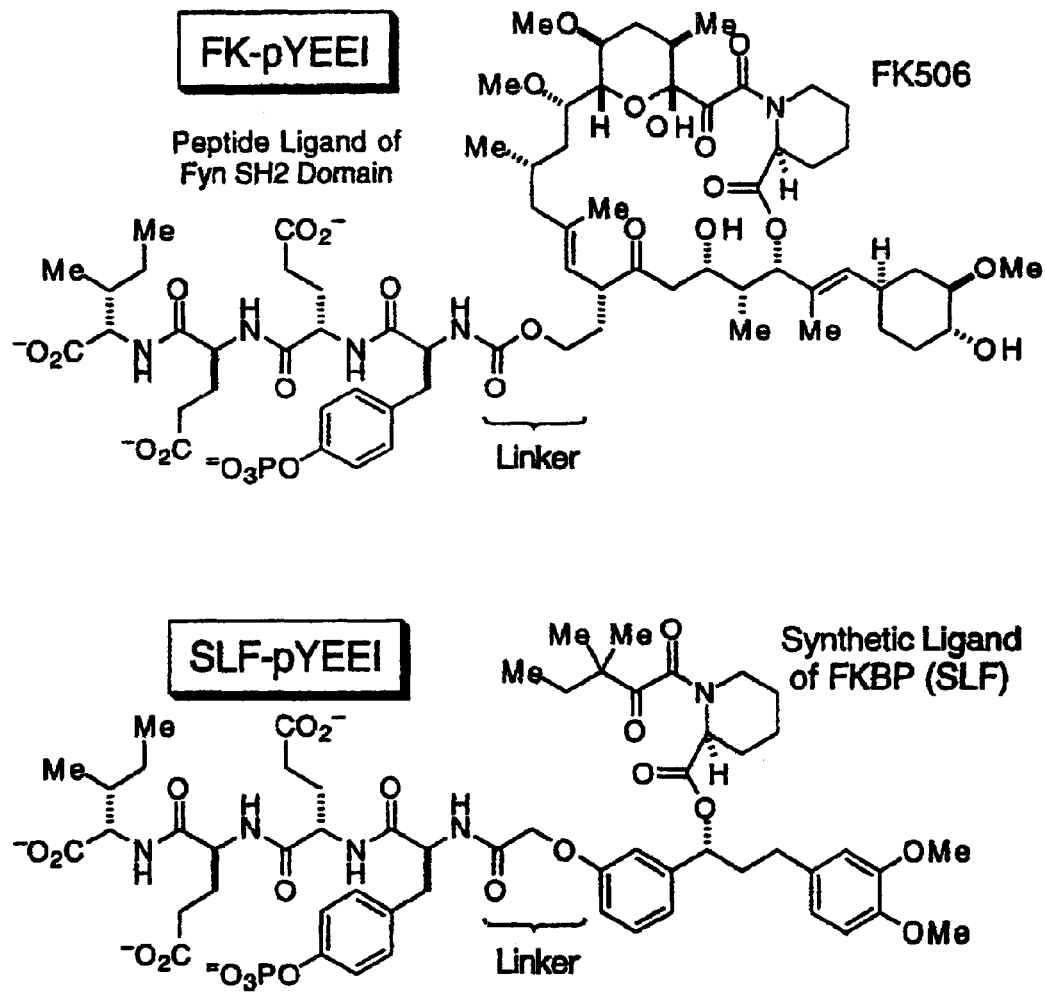
FIG. 2 provides the structures of FKpYEEI and SLFpYEEI.

The pYEEI peptide was chemically linked to FK506 in order to create the bifunctional ligand, FKpYEEI (FIG. 2). The FK506 moiety can be bound by the family of FK506 binding proteins, the FKBPs, which serve as the presenter proteins in the experiments described below. The synthesis of FKpYEEI is based on reacting an activated form of FK506, a mixed carbonate, with the primary amino group of pYEEI. The preparation of the mixed carbonate involves several oxidation steps. To protect the two hydroxy groups from oxidation, a sample of FK506 was reacted with tert-butyldimethylsilyl triflate (TBSOTf) in the first reaction. A 10-mL vial was charged with FK506 (32 mg, 40 mol), 2,6-lutidine (47 L, 400 mol, 10 eq), TBSOTf(47 L, 200 mol, 5 eq) and 3 mL of distilled dichloromethane. The reaction was stirred under an atmosphere of nitrogen for 45 min, starting at 0° C. and letting it warm to room temperature. To quench any excess TBSOTf, 25 eq of methanol (40 L) was added and the reaction was stirred at room temperature for 25 minutes. The reaction was extracted twice with 10 mL DCM in the presence of 10 mL aqueous sodium bicarbonate. The organic phase, containing 24,32-bis [(tert-butyldimethylsilyl)oxy]-FK506 (FK506-TBS2), was dried with magnesium sulfate and subsequently, filtered and evaporated to an oil. The product was purified by flash chromatography using a mixture of hexane and ethyl acetate (5:1 to 3:1). The fractions containing FK506-TBS2 were combined and evaporated. The yield was 35 mg.

2. Osmylation and Oxidative Cleavage

A 10 mL flask was charged with FK506-TBS2 (32 mg, 31 mol), 4-methylmorpholine N-oxide (21 mg, 155 mol), water (50 L) and tetrahydrofuran (THF) (2 mL). Osmium tetroxide (26 L, 3.1 mol, 0.12 M solution in water) was added via syringe. The clear colorless solution was stirred at room temperature for 4.0 h. The reaction was diluted with 50% aqueous methanol (1 mL) and sodium periodate (66 mg) was added in one portion. The cloudy mixture was stirred 25 min at room temperature, diluted with ether (10 mL), and washed with a saturated aqueous sodium bicarbonate solution (10 mL). The phases were separated and the aqueous layer was back-extracted with ether (2×10 mL) The combined organic layers were dried over $MgSO_4$ and solid sodium sulfite (50 mg). The organic phase was then filtered and concentrated.

3. Reduction

The aldehyde 1 was immediately dissolved in THF (2 mL) and cooled to −78° C. under an atmosphere of nitrogen, and treated with lithium tris[(3-ethyl-3-pentyl)oxy]aluminum hydride (63 L, 8.8 mol, 1 eq). The clear solution was stirred for 60 min at −78° C., then quenched with ether (3 mL) and saturated aqueous ammonium chloride (200 L). The mixture was allowed to warm to room temperature and solid sodium sulfate was added to dry the solution. The mixture was stirred 20 min, filtered, concentrated, and the resulting oil was immediately dissolved in acetonitrile (2 mL).

4. Mixed Carbonate

To the solution of the primary alcohol 2 in acetonitrile (2 mL) was added 2,6-lutidine (36 1, 0.31 mmol, 10 eq) and N,N'-disuccinimidyl carbonate (40 mg, 0.16 mmol, 5 eq). The heterogenous mixture was stirred at room temperature for 19 h, at which time the solution was diluted with ether (10 mL) and washed with saturated aqueous sodium bicarbonate (5 mL). The aqueous solution was back-extracted with ether (2×10 mL). The organic phases were combined and dried ($MgSO_4$), concentrated and subjected to flash chromatography (3:1 to 2:1 to 1:1 hexane/ethyl acetate). The desired mixed carbonate 3 was isolated as a clear, colorless oil (7.1 mg, 6 mmol).

5. Coupling of the pYEEI peptide

A 1 mL-vial was loaded with the mixed carbonate (7 mg, 5.95 mol), pYEEI peptide (7.7 mg. 11.9 mol, 2 eq) and triethylamine (21 L, 119 mol, 20 eq) together with dimethylformamide (400 L). The reaction was stirred at room temperature for 24 h. For the deprotection of TBS2-

FKpYEEI, the reaction was transfered into a 1.5 mL polypropylene eppendorf tube. Acetonitrile (100 L) was added to bring the reaction volume to 500 L. Then, hydrofluoric acid (55 L) was pipeted into the reaction. The reaction was stirred for 16 h and, then, quenched with triethylamine (160 L). The reaction mixture was lyophilized to a yellow oil. The oil was taken up in 33% aqueous acetonitrile and 0.1% trifluoroacetic acid. The separation of FKpYEEI from unreacted peptide was achieved by HPLC (column: Supelco LC-18 C18, 100 Å). By amino acid analysis it was found that the yield of the synthesis was 1 mg of FKpYEEI.

B. Synthesis of SLFpYEEI

SLF was synthesized according to the procedures of Holt et al. [J. Am. Chem. Soc. 1993, 115, 9925]. SLF was coupled to the N-terminus of the resin-bound protected pYEEI peptide using PyBOP. The heterodimeric SLFpYEEI was deprotected and cleaved from the Novasyn TGT resin (Calbiochem-Novabiochem, San Diego, Ca.) using 25% trifluoroacetic acid and 2.5% triisopropyl silane in methylene chloride and the desired product was isolated using reverse phase HPLC. C. Recombinant FKBPs As presenter proteins, we used FKBP12 and FKBP52, two FKBPs that bind FK506 with high affinity (0.4 nM and 44 nM, respectively). Recombinant FKBP12 or FKBP52 bind to the FK506 moiety of FKpYEEI, thus creating an enlarged binding surface. Recombinant FKBP12 was expressed as a GST fusion protein and bound to glutathione beads (Pharmacia). Using thrombin (Sigma) to cleave the GST-FKBP12 fusion protein at a thrombin cleavage site in the linker between GST and FKBP12, recombinant FKBP12 could be released from the glutathione beads where GST remained bound. FKBP52 was expressed with a tag of six histidine residues at its N-terminus (pET28c expression vector, Novagen). The recombinant protein was bound via the histidine tag to $Ni^{2+}$ NTA agarose beads (Qiagen), washed extensively and eluted with imidazole. The FKBP52 elution buffer was dialyzed over night against the buffer used in the binding reactions (20 mM Tris pH 7.2, 150 mM NaCl). In order to establish the affinity of the FKBP-FKpYEEI complex for the three SH2 domains, the following competition assay was developed.

D. The Assay

The pYEEI peptide was coupled to Affi-Gel 10 beads (Biorad) via its amino-group. The Fyn, Lck and PLC SH2 domains were expressed in bacteria as GST fusion proteins. The linker between the GST protein and the SH2 domain contained a thrombin cleavage site and a protein kinase A (PKA) phosphorylation site. The fusion protein on glutathione beads was radioactively labeled at the PKA phosphorylation site using PKA (Sigma). After extensive washing of the beads, the radioactive SH2 domain was released by cleavage with thrombin (Sigma). In a typical binding assay, 7.5 L of a 1:1 peptide bead slurry were incubated with the radioactive SH2 domain (200 nM) for 2 hours in 100 L of binding buffer (20 mM Tris pH7.2; 150 mM NaCl). In order to separate the radioactive protein bound to the beads, the binding reaction was transfered into a PCR tube (USA Scientific Plastic), whose bottom had been punctured with a 26gauge needle. The PCR tube was placed in a 0.5 mL Eppendorf tube which in turn was placed in a regular 1.5 mL Eppendorf tube. The tubes were spun for 1 second at maximal speed in an Eppendorf centrifuge resulting in the separation of the beads remaining in the PCR tube and the supernatant, which was collected in the 0.5 ml Eppendorf tube. The beads were resuspended in 100 L PBS and the radioactivity was counted in a liquid scintillation counter after addition of 3 ml scintillation fluid. The radioactivity remaining in the 100 L supernatant was counted in the same way. It was determined that under the conditions described 65% Fyn, 25% PLC and 15%Lck SH2 domain were bound to the beads. By increasing the amount of beads, up to 80% Fyn, 40% PLC and 25% Lck could be bound. These amounts reflect the active fraction of SH2 domains in the different protein preparations. There was no indication that the inactive protein fraction interfered with the binding assay.

1. Experiments:

SLFpYEEI and FKpYEEI are bifunctional molecules that can bind FKBP12 and FKBP52 as well as the Fyn SH2 domain (FIG. 2). The binding constants (Kd values) of the bifunctional molecules for the three proteins were measured using isothermal titration calorimetry (ITC) (Table 1).

TABLE 1

Binding Constants (Kds) for Interacting Partners Used in this Study

| | FKpYEEI | SLFpYEEI | SLF | FK506 |
|---|---|---|---|---|
| FKBP12 | 45 nM | 61 nM | 20 nM | 0.4 nM |
| FKBP52 | 150 nM | 5 M | 3 M | 44–66 nM |
| Fyn SH2 domain | 520 nM | 183 nM | n.d. | n.d. |

Figure 3:
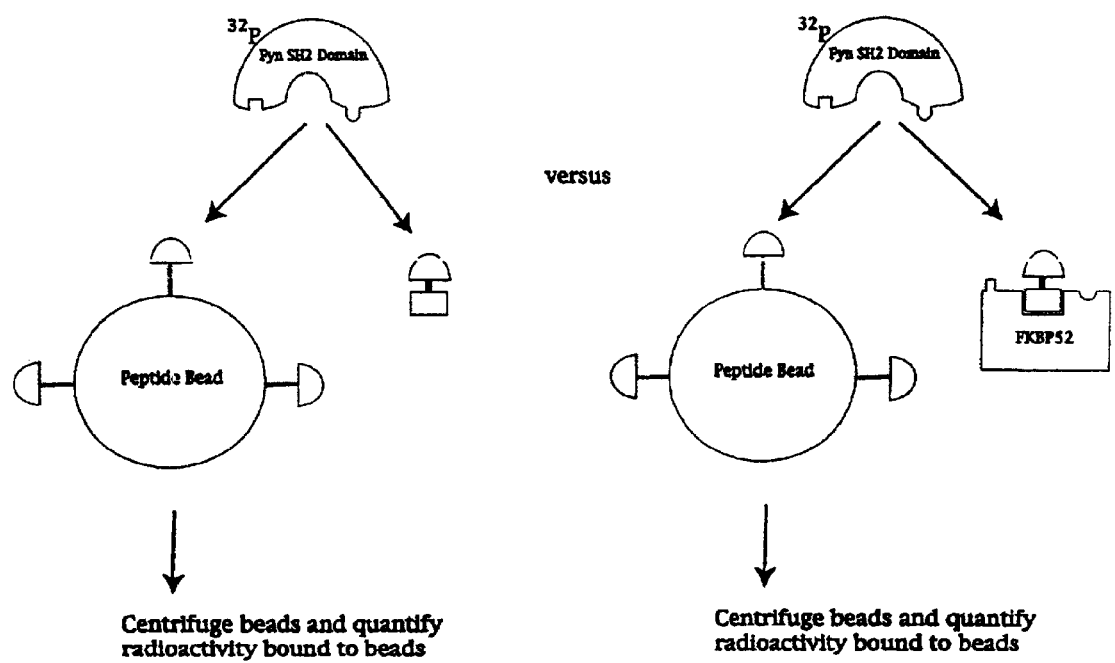
FIG. 3 provides a representation of a competition binding assay of Fyn-SH2 domain to pYEEI beads in the presence of FKpYEEI and FKpYEEI plus FKBP52.

The binding constants of FKBP12, FKBP52, and Fyn for SLF, SLFpYEEI and FKpYEEI were determined using an Omega Isothermal Titration Calorimeter (Microcal, Northampton, Ma.). Protein in aqueous buffer (20–60 M, pH 7.2, 150 mM NaCl, 20 mM Tris) was equilibrated in the microcalorimeter cell at 25° C. for 1–2 hr after being degassed for 10 min. Ligand, in identical buffer as protein (170–600 M), was taken into a 250 L syringe after being degassed for 10 min. The syringe was loaded into the cell, spun at 400 rpm and allowed to equilibrate for 1–2 hr. Ligand was injected into the cell (25 × 10 L, 6 min apart) and the heat evolved was quantitated. Binding constants were calculated from a numerical fit to the experimental data as described in (Wiseman et al., Anal. Biochem. (1989), 179, 131).
n.d.: not determined In order to determine the relative affinity of the SH2 domains for FKpYEEI or SLFpYEEI alone and FKpYEEI or SLFpYEEI bound to FKBP12 and FKBP52, the following competition assay was used. Radioactive SH2 domains were incubated with pYEEI peptide beads and FKpYEEI or SLFpYEEI in the presence or absence of the respective FKBP proteins. FKpYEEI and FKpYEEI/FKBP as well as SLFpYEEI and SLFpYEEI/FKBP compete for binding of the SH2 domains with the peptide beads. The higher the affinity of the FKpYEEI or SLFpYEEI ligand in the supernatant, the less SH2 domain is bound to the peptide beads (FIG. 3).

The following experiments suggest that the formation of a binary complex between an endogenous protein like FKBP and a bifunctional molecule like FKpYEEI or SLFpYEEI can enhance the affinity, the specificity and selectivity of a small molecule ligand such as the pYEEI peptide.

a. Affinity Enhancement i. In the presence of FKBP52, FKpYEEI can Bind the Fyn SH2 Domain with Higher Affinity.

Figure 4:
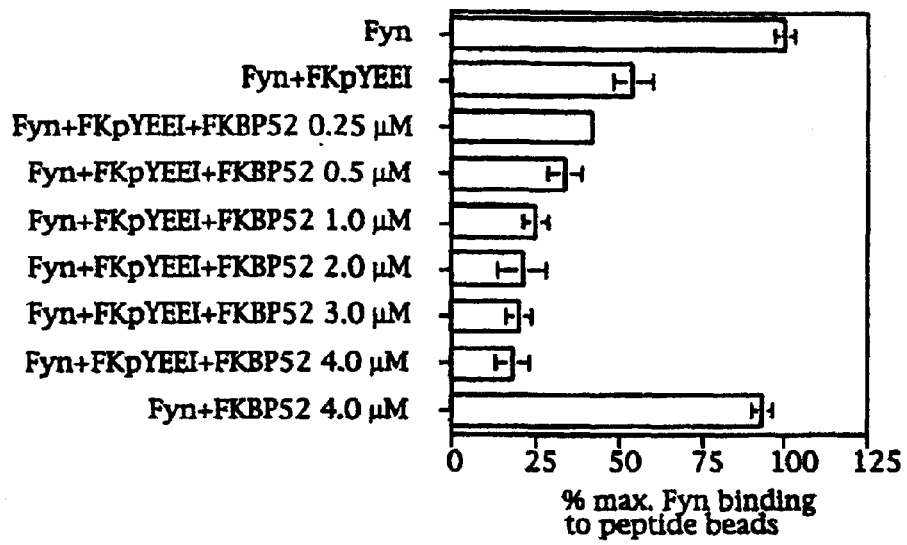
FIG. 4 shows the results from a competition binding assay of the Fyn-SH2 domain to pYEEI beads in the presence of FKpYEEI and FKpYEEI plus FKBP52.

Using the competition binding assay described above, FKpYEEI was added to peptide beads and the Fyn SH2 domain in the presence of increasing concentrations of FKBP52 (FIG. 4). In this assay, in 100 L binding reactions, radioactively labeled Fyn SH2 domain (200 nM) was incubated with 7.5 L of a 1:1 pYEEI bead slurry. No FKpYEEI, 1.0 M FKpYEEI or 1.0 M FKpYEEI plus increasing concentrations of FKBP52 (0.25–4.0 M) were added. The binding reactions were rotated at room temperature for 2 hours. The supernatant was separated from the beads by spinning the binding reactions in punctured PCR tubes for 1 sec in an Eppendorf centrifuge at maximal speed. The beads were resuspended in 100 1 PBS and the radioactivity bound to the beads was counted in a liquid scintillation vial for 30 sec. The radioactivity bound to the beads in the presence of only the Fyn SH2 domain was plotted as 100% of maximal Fyn SH2 domain binding to pYEEI beads. The radioactivity bound in the presence of FKpYEEI and FKBP52 was calculated as the percentage of maximal Fyn SH2 domain binding. Every binding reaction was done in triplicate. The data points reflect the average of the three binding reactions. The error bars indicate the standard error.

The results show that as more FKBP52 is present, less Fyn is bound by the peptide beads. FKpYEEI binds to FKBP52 and forms a binary complex. In the context of this binary complex, FKpYEEI has a higher affinity for the Fyn SH2 domain which is reflected in the decreasing amounts of Fyn SH2 domain binding to peptide beads.

ii. FK506 Reverses the FKBP52 Effect

Figure 5:
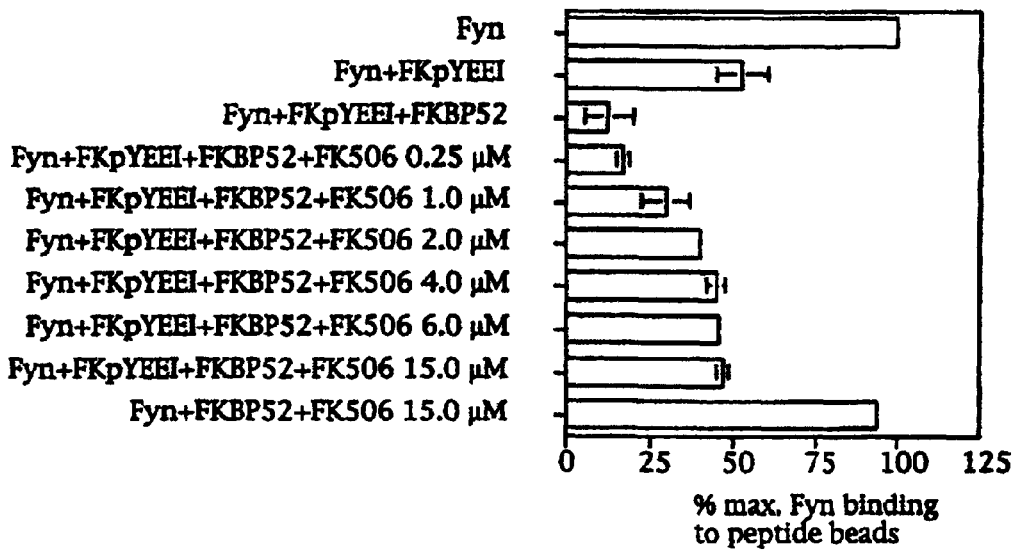
FIG. 5 shows the results from a competition binding assay of the Fyn SH2 domain to pYEEI beads in the presence of FKpYEEI, FKpYEEI plus FKBP52 and FKpYEEI plus FKBP52 plus FK506.

To verify that the affinity enhancing effect is based on a binary complex formed by FKpYEEI binding to the FK506 binding pocket of FKBP52, increasing concentrations of FK506 were added to the binding reaction containing the Fyn SH2 domain, FKpYEEI and FKBP52 (FIG. 5). In this assay, in 100 L binding reactions, radioactively labeled Fyn SH2 domain (200 nM) was incubated with 7.5 L of a 1:1 pYEEI bead slurry. FKpYEEI (1.0 M), FKpYEEI (1.0 M) plus FKBP52 (2.0 M) and FKpYEEI (1.0 M) plus FKBP52 (2.0 M) plus increasing concentrations of FK506 (0.25–15.0 M) were added. The binding reactions were rotated at room temperature for 2 hours, centrifuged and analysed as described above.

Figure 6:
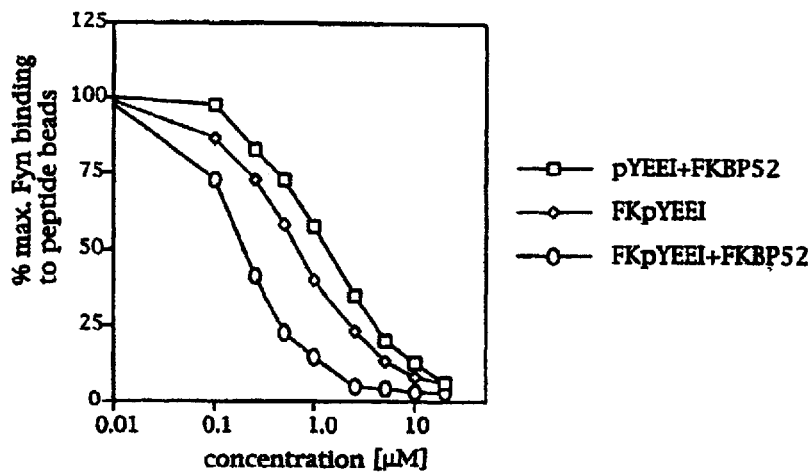
FIG. 6 shows the results from a competition binding assay of the Fyn SH2 domain to pYEEI beads at various concentrations of pYEEI and FKpYEEI in the presence and absence of FKBP52.

The results show that as the concentration of FK506 increases, the affinity enhancing effect of FKBP52 is reversed. Free FK506 binds to the FK506 binding pocket of FKBP52 with higher affinity than FKpYEEI (see Table 1). Therefore, the loss of the affinity enhancing effect is due to the dissociation of the binary complex formed between FKBP52 and FKpYEEI.

iii. The Presence of FKBP52 Increases the Affinity of FKpYEEI for the Fyn SH2 Domain by Three-Fold FIG. 6 is a graph of the competition binding curves for the Fyn SH2 domain and FKpYEEI as well as the Fyn SH2 domain and the peptide pYEEI in the absence and the presence of FKBP52. Fyn SH2 domain was incubated with peptide beads and increasing concentrations of FKpYEEI in the absence or presence of FKBP52. Specifically, in this assay, in 100 L binding reactions, radioactively labeled Fyn SH2 domain (200 nM) was incubated with 7.5 L of a 1:1 pYEEI bead slurry. Increasing concentrations of FKpYEEI or pYEEI (0.1–20.0 M) were added in the presence or absence of FKBP52 (4.5 M). The binding reactions were rotated at room temperature for 2 hours, centrifuged and analysed as described above. Half maximal binding (IC50) is observed at 750 riM FKpYEEI in the absence of FKBP52. In the presence of FKBP52, the IC50 value is 250 riM. Hence, in a complex with FKBP52, the affinity of FKpYEEI for the Fyn SH2 domain is enhanced by a factor of three. The IC50 of the peptide pYEEI is 1.1 M. Hence, FKpYEEI in the context of FKBP52 shows a 4.4 fold enhancement of affinity in respect to pYEEI. Using ITC, the binding constant (Kd) for Fyn SH2 domain binding to the FKpYEEI-FKBP52 complex was determined. The Kd value for this binding event is 130 nM. This is a fourfold enhancement over the Kd of Fyn SH2 domain binding to FKpYEEI alone (Table 1) and this result confirms the data obtained from the competition binding assay.

iv. The Presence of FKBP12 does not Increase the Affinity of FKpYEEI for the Fyn SH2 Domain.

Figure 7:
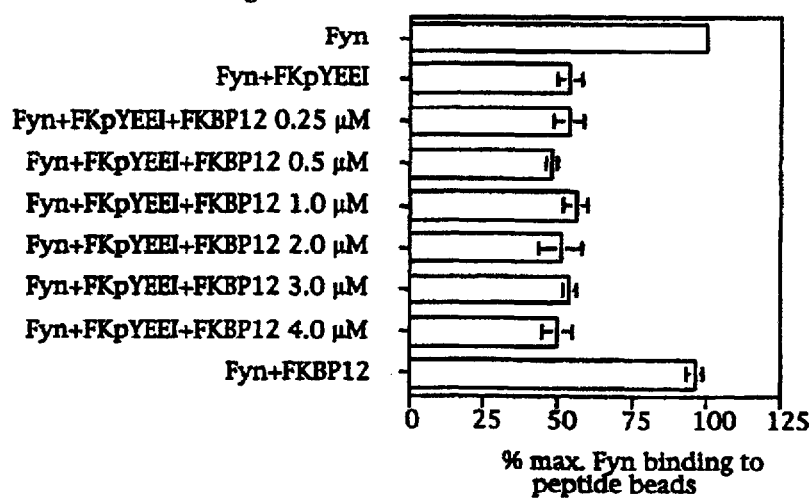
FIG. 7 shows the results from a competition binding assay of the Fyn SH2 domain to pYEEI beads in the presence of FKpYEEI and FKpYEEI plus FKBP12.

The structure of the FK506 binding domain of FKBP52 is very similar to the structure of FKBP12 (Craescu et al., Biochemistry 1996, 35, 11045). To test if the observed affinity enhancement can be achieved by the formation of a binary complex with FKBP12, increasing concentrations of FKBP12 were added to binding reactions containing the Fyn SH2 domain and FKpYEEI (FIG. 7). In this assay, in 100 L binding reactions, radioactively labeled Fyn SH2 domain (200 nM) was incubated with 7.5 L of a 1:1 pYEEI bead slurry. No FKpYEEI, 1.0 M FKpYEEI or 1.0 M FKpYEEI plus increasing concentrations of FKBP12 (0.25–4.0 M) were added. The binding reactions were rotated at room temperature for 2 hours, centrifuged and analysed as described above. The results indicate that the formation of a binary complex between FKpYEEI and FKBP12 does not enhance the binding affinity for the Fyn SH2 domain.

Figure 8:
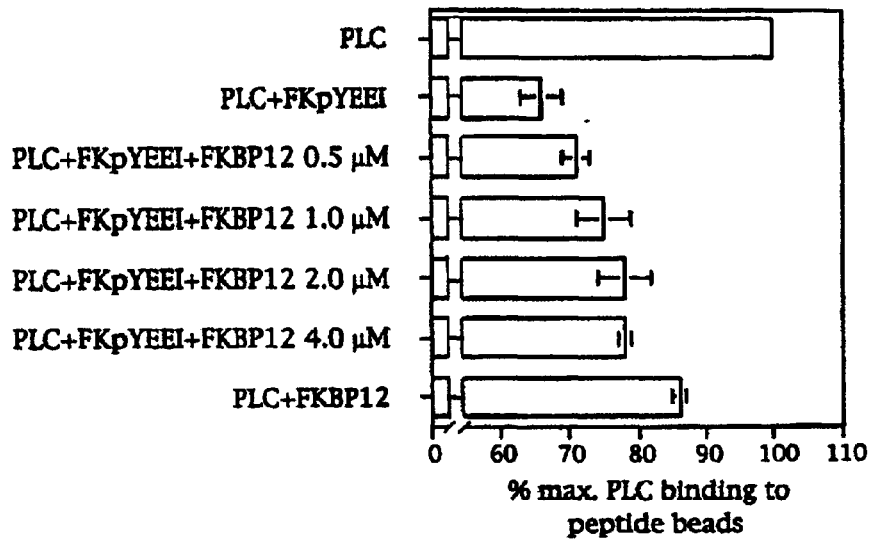
FIG. 8 shows the results from a competition binding assay of the PLC SH2 domain to pYEEI beads in the presence of FKpYEEI and FKpYEEI plus FKBP12.

In summary, the above experiments show that a binary complex of FKBP52 and FKpYEEI binds to the Fyn SH2 domain with a higher affinity than FKpYEEI or pYEEI alone. Since FKBP12 binds FKpYEEI in the same way as FKBP52 but does not support this effect, the increase in affinity must be based on favorable protein—protein interactions between the Fyn SH2 domain and FKBP52.

b. Specificity Enhancement i. FKBP12 Reduces the Affinity of FKpYEEI for the PLC SH2 Domain The binary complex of FKpYEEI and FKBP 12 has the same affinity for the Fyn SH2 domain as free FKpYEEI (see FIG. 7). To test if the FKpYEEI-FKBP12 complex has an effect on the binding of the PLC SH2 domain, increasing concentrations of FKBP12 were added to binding reactions containing the PLC SH2 domain and FKpYEEI (FIG. 8). In this assay, in 100 L binding reactions, radioactively labeled PLC SH2 domain (400 nM) was incubated with 7.5 L of a 1:1 pYEEI bead slurry. No FKpYEEI, 1.0 M FKpYEEI or 1.0 M FKpYEEI plus increasing concentrations of FKBP12 (0.5–4.0 M) were added. The binding reactions were rotated at room temperature for 2 hours, centrifuged and analysed as described above. The results show that as the amount of FKBP12 increases, more PLC SH2 domain binds to the peptide beads. Hence, the binary complex of FKpYEEI-FKBP12 has a decreased affinity for the PLC SH2 domain as compared to free FKpYEEI.

ii. The Reduction in Affinity of FKpYEEI for the PLC SH2 Domain in the Presence of FKBP12 is Reversed by FK506.

Figure 9:
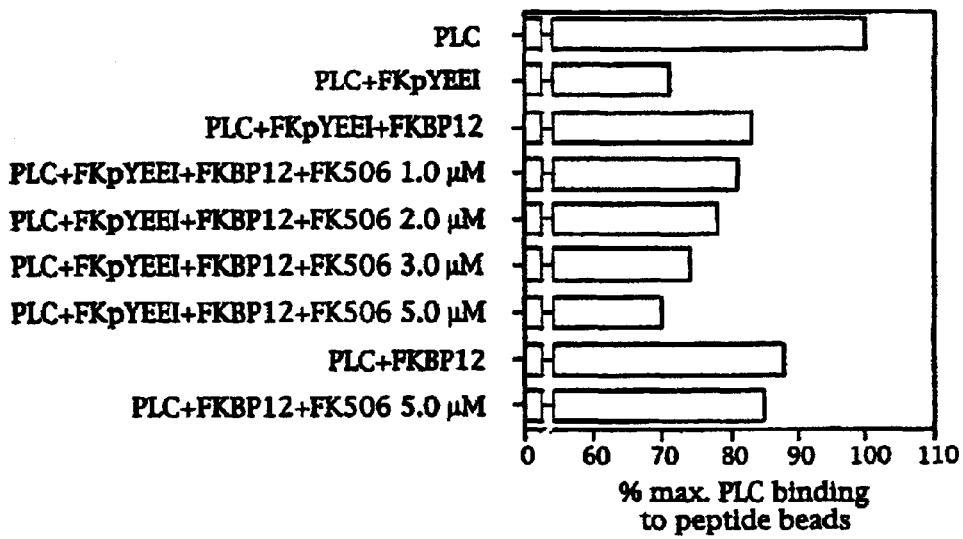
FIG. 9 shows the results from a competition binding assay of the PLC SH2 domain to pYEEI beads in the presence of FKpYEEI, FKpYEEI plus FKBP12 and FKpYEEI plus FKBP12 plus FK506.

To test if the reduction of affinity is due to FKpYEEI binding in the FK506 binding pocket of FKBP12, increasing concentrations of FK506 were added to binding reactions containing the PLC SH2 domain, FKpYEEI and FKBP12 (FIG. 9). In this assay, in 100 L binding reactions, radioactively labeled PLC SH2 domain (400 nM) was incubated with 7.5 L of a 1:1 pYEEI bead slurry. FKpYEEI (1.5 M), FKpYEEI (1.5 M) plus FKBP12 (2.0 M) and FKpYEEI (1.5 M) plus FKBP12 (2.0 M) plus increasing concentrations of FK506 (1.0–5.0 M) were added. The binding reactions were rotated at room temperature for 2 hours, centrifuged and analysed as described above. The results show that as the concentration of FK506 increases, the affinity reduction is reversed. Hence, the loss of affinity of FKpYEEI for the PLC SH2 domain is dependent on the formation of the binary complex with FKBP12. This suggests that unfavorable protein—protein contacts between FKBP12 and the PLC SH2 domain are the basis for the reduced binding.

iii. The Binary FKBP 12-FKpYEEI Complex Reduces the Affinity of FKpYEEI for the PLC SH2 Domain but not for the Fyn or Lck SH2 Domain.

Figure 10:
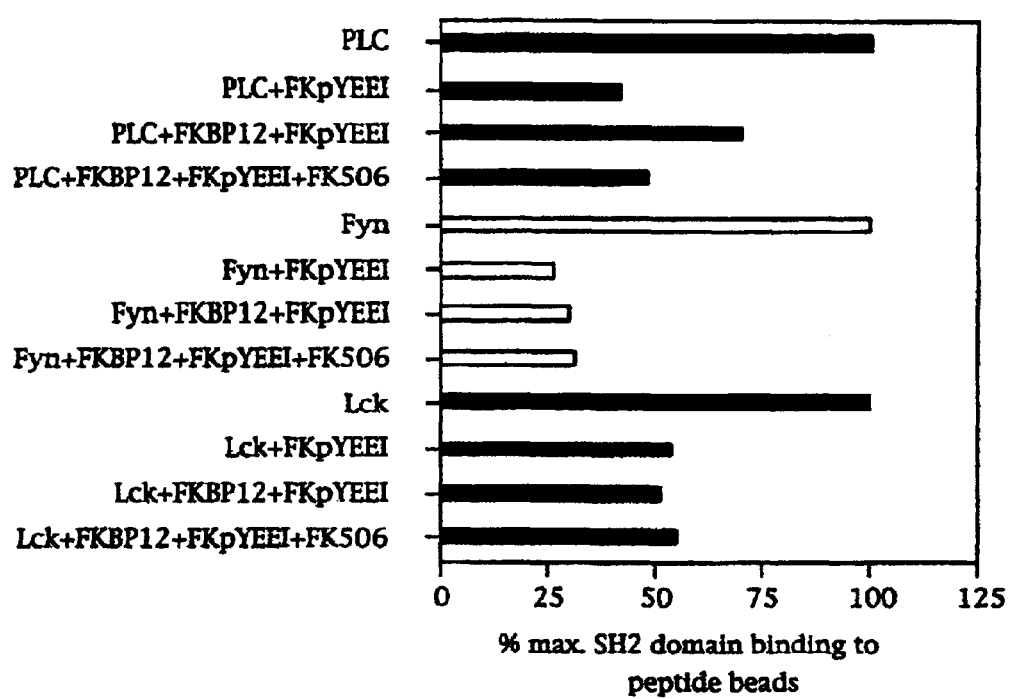
FIG. 10 shows the results from a competition binding assay of the Fyn, Lck and PLC SH2 domains to pYEEI beads in the presence of FKpYEEI, FKpYEEI plus FKBP12 and FKpYEEI plus FKBP12 plus FK506.

To test if the presence of FKBP12 affects the affinity of FKpYEEI for other SH2 domains aside from the PLC SH2 domain, FKpYEEI and FKBP12 were added to binding reactions containing the Fyn, Lck or PLC SH2 domains (FIG. 10). In this assay, 100 L binding reactions, radioactively labeled PLC SH2 domain (200 nM), Lck SH2 domain (800 nM) and Fyn SH2 domain (200 nM) was incubated with 7.5 L of a 1:1 pYEEI bead slurry. FKpYEEI (1.5 M), FKpYEEI (1.5 M) plus FKBP12 (2.0 M) and FKpYEEI (1.5 M) plus FKBP12 (2.0 M) plus FK506 (4.0 M) were added to the PLC SH2 domain reactions. FKpYEEI (1.0 M), FKpYEEI (1.0 M) plus FKBP12 (2.0 M) and FKpYEEI (1.0 M) plus FKBP12 (2.0 M) plus FK506 (4.0 M) were added to the Lck and Fyn SH2 domains. The binding reactions were rotated at room temperature for 2 hours, centrifuged and analysed as described above. The results show that the FKpYEEI-FKBP12 complex does not affect the affinity of FKpYEEI for the Fyn or Lck SH2 domain. Hence, the FKpYEEI-FKBP12 complex creates specificity by supporting the binding of the Fyn and Lck SH2 domains while reducing binding to the PLC SH2 domain.

In summary, the above experiments show that the formation of a binary complex may lead to unfavorable protein—protein interactions between the presenter protein and some targets but not other targets of the drug. Therefore, the formation of a complex between a bifunctional molecule and a presenter protein can be used to create specificity.

c. Selectivity Enhancement i. FKBP 12 Reduces the Affinity of SLFpYEEI for the Fyn SH2 Domain.

Figure 11:
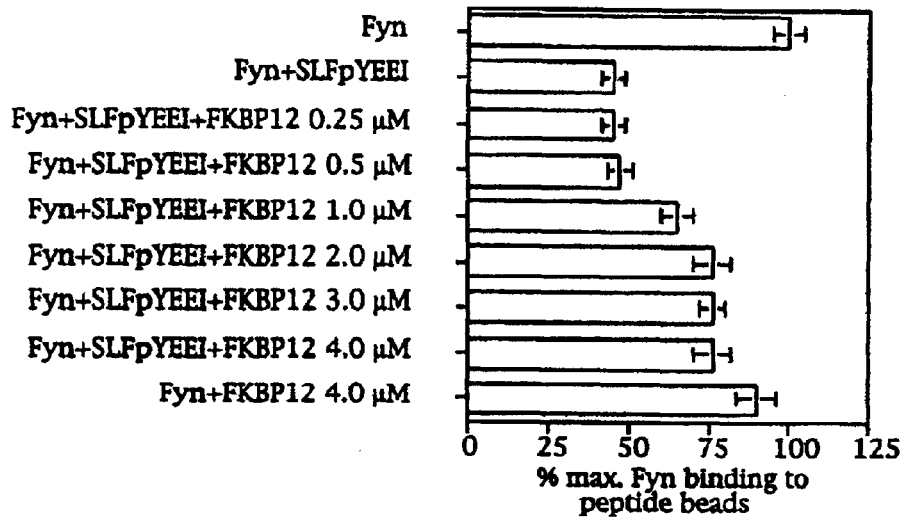
FIG. 11 shows the results from a competition binding assay of the Fyn SH2 domain in the presence of SLFpYEEI and SLFpYEEI plus FKBP12.

In comparison to FKpYEEI, SLFpYEEI presents the pYEEI peptide in a different orientation and in a different distance in respect to the FKBP12 protein surface. To test if the binary SLFpYEEI-FKBP12 complex affects binding of the Fyn SH2 domain differently than free SLFpYEEI, increasing concentrations of FKBP12 were added to binding reactions containing SLFpYEEI and the Fyn SH2 domain (FIG. 11). In this assay, in 100 L binding reactions, radioactively labeled Fyn SH2 domain (200 nM) was incubated with 7.5 L of a 1:1 pYEEI bead slurry. SLFpYEEI (1.0 M) and SLFpYEEI (1.0 M) plus increasing concentrations of FKBP12 (0.25–4.0 M) were added. The binding reactions were rotated at room temperature for 2 hours, centrifuged and analysed as described above. The addition of FKBP12 increases the amount of Fyn SH2 domain binding to peptide beads. This indicates that the SLFpYEEI-FKBP12 complex shows reduced affinity for the Fyn SH2 domain.

ii. FK506 Reverses the Effect of Decreased Binding Activity of the SLFpYEEI-FKBP12 Complex.

Figure 12:
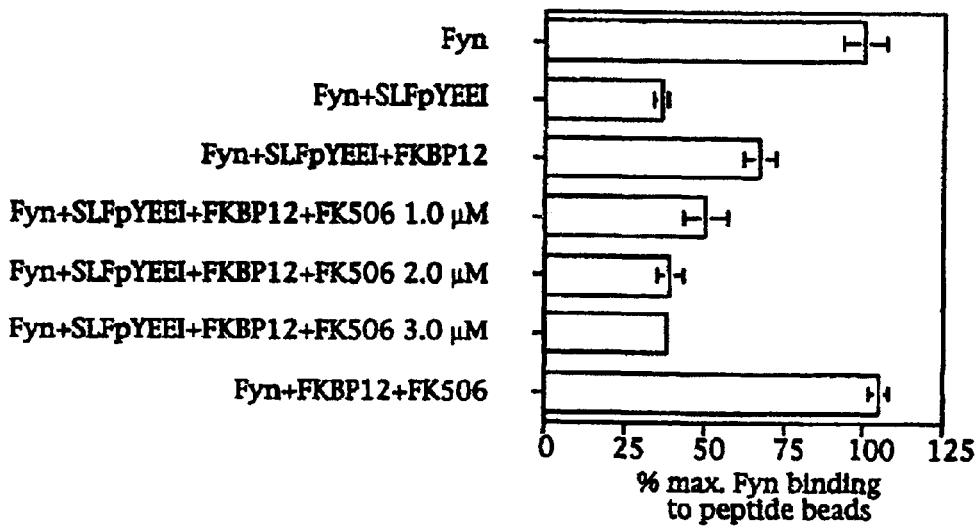
FIG. 12 shows the results from a competition binding assay of the Fyn SH2 domain to pYEEI beads in the presence of SLFpYEEI, SLFpYEEI plus FKBP12 and SLFpYEEI plus FKBP12 plus FK506.
Figure 13:
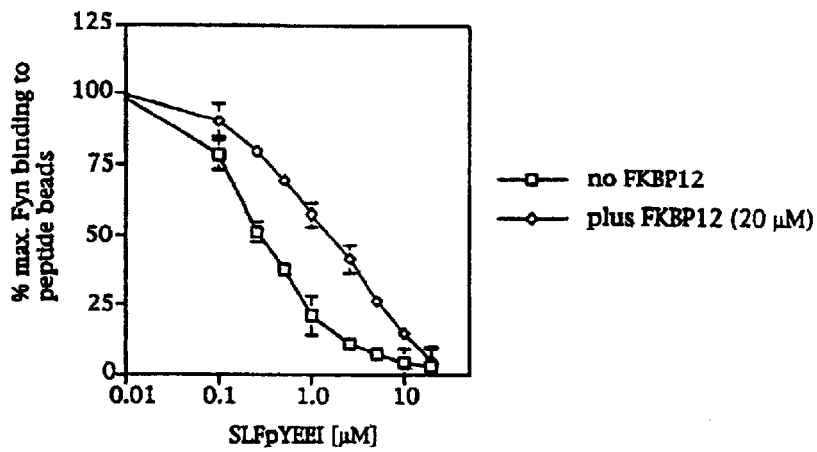
FIG. 13 shows the results from a competition binding assay of the Fyn SH2 domain to pYEEI beads at increasing concentrations of SLFpYEEI in the presence and absence of FKBP12.

To verify that the reduced affinity of the Fyn SH2 domain is based on SLFpYEEI binding to the FK506 binding pocket of FKBP12, increasing concentrations of FK506 were added to binding reactions containing Fyn SH2 domain, SLFpYEEI and FKBP12 (FIG. 12).In this assay, in 100 L binding reactions, radioactively labeled Fyn SH2 domain (200 nM) was incubated with 7.5 L of a 1:1 pYEEI bead slurry. SLFpYEEI (1.0 M) and SLFpYEEI (1.0 M) plus FKBP12 (2.0 M) and SLFpYEEI (1.0 M) plus FKBP12 plus increasing concentrations of FK506 (1.0–3.0 M) were added. The binding reactions were rotated at room temperature for 2 hours, centrifuged and analysed as described above. FK506 reverses the effect of reduced affinity of SLFpYEEI for the Fyn SH2 domain in the presence of FKBP12. Hence, the binary complex of SLFpYEEI and FKBP 12 establishes unfavorable protein—protein interactions between FKBP 12 and the Fyn SH2 domain so that the affinity, with which the binding event is taking place, is reduced.

iii. The Presence of FKBP12 Decreases the Affinity of SLFpYEEI for the Fyn SH2 Domain by Six-Fold FIG. 13 is a graph of the competition binding curves for the Fyn SH2 domain and SLFpYEEI in the absence and the presence of FKBP12. Fyn SH2 domain was incubated with increasing concentrations of SLFpYEEI in the absence or presence of FKBP12. In this assay, in 100 L binding reactions, radioactively labeled Fyn SH2 domain (200 nM) was incubated with 7.5 L of a 1:1 pYEEI bead slurry. Increasing concentrations of SLFpYEEI (0.1–20.0 M) were added in the presence or absence of FKBP12 (20 M). The binding reactions were rotated at room temperature for 2 hours, centrifuged and analysed as described above. Half maximal binding (IC50) is observed at 0.25 M SLFpYEEI in the absence of FKBP12. In the presence of FKBP12, the IC50 value is 1.5 M. Hence, in a complex with FKBP12, the affinity of SLFpYEEI for the Fyn SH2 domain is reduced by a factor of six. This effect was confirmed by ITC. The Kd of Fyn SH2 domain binding to free SLFpYEEI is 183 nM (Table 1) and the Kd for binding of the SLFpYEEI-FKBP12 complex is 1.5 M.

iv. The SLF YEEI-FKBP12 Complex Shows Reduced Binding to the Fvn as well as the Lck and PLC SH2 Domains.

Figure 14:
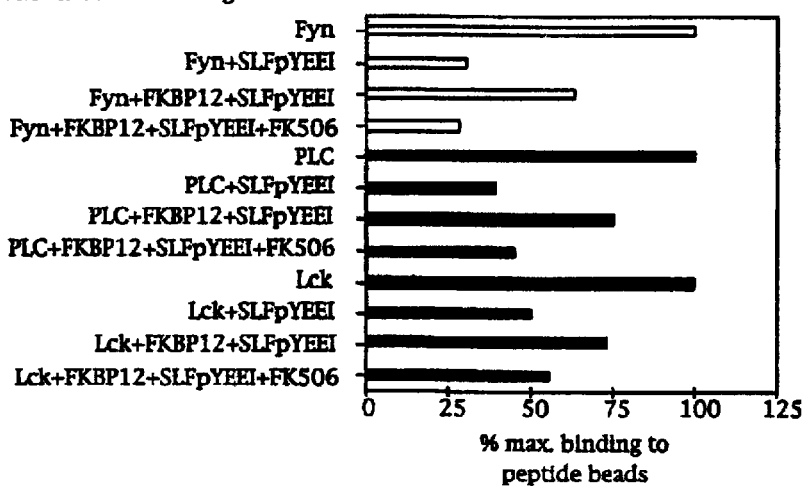
FIG. 14 shows the results from a competition binding assay of the Fyn, Lck and PLC SH2 domains in the presence of SLFpYEEI, SLFpYEEI plus FKBP 12 and SLFpYEEI plus FKBP12 plus FK506.

To test if the PLC and the Lck SH2 domains bind to SLFpYEEI-FKBP12 with reduced affinity, these SH2 domains together with the Fyn SH2 domain were incubated with SLFpYEEI alone or SLFpYEEI and FKBP12 (FIG. 14). In this assay, in 100 L binding reactions, radioactively labeled Fyn, Lck and PLC SH2 domains (200 nM) were incubated with 7.5 L of a 1:1 pYEEI bead slurry. SLFpYEEI (1.0 M) and SLFpYEEI (1.0 M) plus FKBP12 (2.0 M) and SLFpYEEI (1.0 M) plus FKBP12 (2.0 M) plus FK506 (3.0 M) were added. The binding reactions were rotated at room temperature for 2 hours, centrifuged and analysed as described above. Not only the Fyn SH2 domain, but also the Lck and PLC SH2 domains show reduced binding by the binary complex.

In summary, the above experiments show that the formation of a binary complex may greatly reduce binding of the drug to all of its targets in a cell that contains the presenter molecule. If an organism has cells that contain the presenter protein and other cells that do not contain the presenter, then, the cells lacking the presenter protein will be more affected by the activity of the bifunctional molecule than cells expressing the presenter.

EXAMPLE II

Activity of Penicillamine Para-Amino Salicylic Acid Bifunctional Molecule

To determine whether isoform specificity could be achieved by chemically linking a drug to a ligand for an extracellular protein, we synthesized compound 1 shown below in FIG. 1. Compound 1 consists of a penicillamine moiety coupled via a glycine linker to para-amino salicylic acid, a known ligand for albumin with an IC50 of 5 $\mu$m. Penicillamine is an inhibitor of the enzyme alkaline phosphatase, with IC 50 values in the $\mu$M range for a wide variety of alkaline phosphatase isoforms. We reasoned that by recruiting albumin to the alkaline phosphatase surface using the bifunctional compound 1, we could modulate the effective affinity of penicillamine for its target, alkaline phosphatase.

Structure of Heterodimeric Compound 1

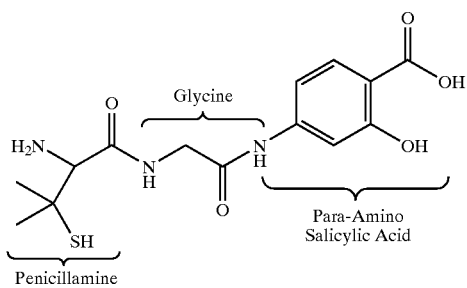

Reactions were conducted in 200 mM diethanolamine buffer, pH 10, with methylumbeliferal phosphate as the substrate. The reaction was monitored by recording fluorescence of the hydrolysis product (excitation at 355 nM, fluorescence at 460 nM), and the first 10% of the reaction was used to determine the rate of the reaction.

The results are tabulated in table 2 below. In the presence of 100 $\mu$M human serum albumin, compound 1 was seen to be a better inhibitor for four of the enzymes tested relative to the inhibition seen in the absence of albumin. For the other eight enzymes tested, no change in the IC50 value was seen in the presence or absence of albumin. IC50 values were seen to decrease roughly 2-fold for the eel intestine and human placenta isoforms of the enzyme, and roughly 12-fold for the rabbit intestine and shrimp isoforms.

TABLE 2

IC50 Values of Compound 1 for Alkaline Phosphatase Isoforms in the Presence and Absence of 100 $\mu$M Human Serum Albumin

| Enzyme Source | IC50 (no albumin) | IC50 (100 $\mu$M albumin) |
| --- | --- | --- |
| Calf Intestine | 20 $\mu$M | 20 $\mu$M |
| Rabbit Intestine | 300 $\mu$M | 25 $\mu$M |
| Bacteria | 50 $\mu$M | 50 $\mu$M |
| Dog Intestine | 20 $\mu$M | 20 $\mu$M |
| Porcine Kidney | 50 $\mu$M | 50 $\mu$M |
| Guinea Pig Intestine | 80 $\mu$M | 80 $\mu$M |
| Eel Intestine | 110 $\mu$M | 70 $\mu$M |
| Porcine Intestinal Mucosa | 50 $\mu$M | 50 $\mu$M |
| Bovine Milk | 50 $\mu$M | 50 $\mu$M |
| Human Placenta | 300 $\mu$M | 45 $\mu$M |
| Shrimp | 3 mM | 80 $\mu$M |

EXAMPLE III

Selectivity Experiment-Using bifunctional Molecules to Detoxify Antimicrobials

A. Introduction

Many molecules that contain the 2,4-diaminopteridine bicyclic ring structure are inhibitors of dihydrofolate reductase (DHFR) and these molecules usually possess strong antimicrobial activity. However, the pteridine structure alone is not very attractive for widespread use as an anti-infective because it is a non-selective inhibitor of DHFR: it affects not only microbial DHFR but it also inhibits the human homolog. As a result, treatment of a patient with pteridines often causes side effects and toxicity. In order to reduce the ability of the pteridine nucleus to bind to human DHFR, a pteridine derivative is covalently linked to a ligand of FKBP (e.g. SLF, FK506, etc.). Based on structure-activity relationship (SAR) data, the pteridine and FKBP ligand are linked in such a way that their binding to DHFR and FKBP, respectively, are as little affected as possible.

B. Synthesis

The following provides a representative synthesis protocol for the production of a pteridine-SLF bifunctional compound. Analogous protocols are employed to produce bifunctional compounds of pteridine and other FKBP ligands, such as FK506.

In the case of the pteridines, SAR data suggests that the alkyl position at C6 is the best for derivatization in order not to disrupt binding to DHFR. The co-crystal structure of SLF and FKBP together with SAR data reveals that the best position to derivative SLF is the phenolic hydroxyl group. To obtain a molecule with the desired properties, various linkers are used to connect the pteridine and SLF. Two examples are shown.

The synthesis of two pteridine-SLF bifunctional molecules with two different linkers requires the following reactions:

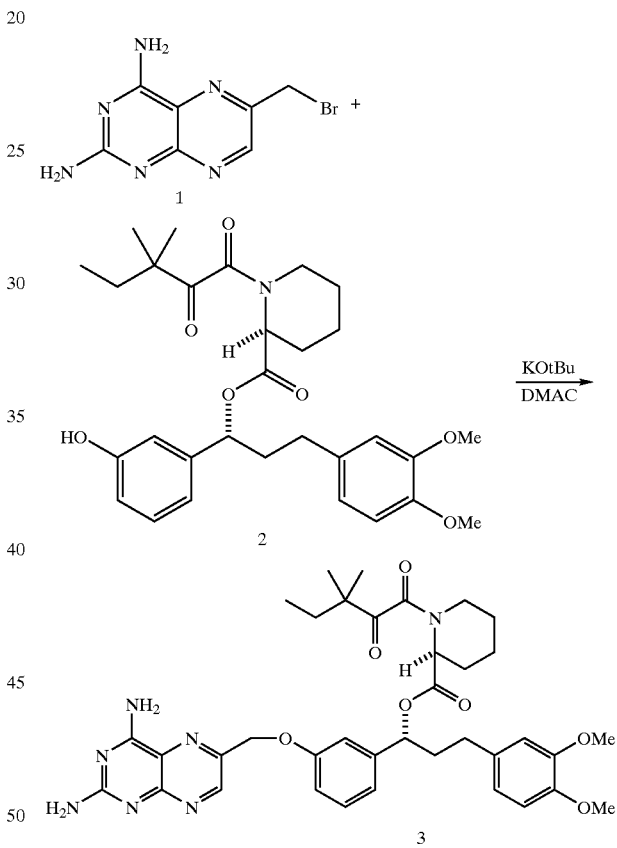

EXAMPLE 1

A solution of 2,4-diamino-6-bromomethylpteridine (1) in dimethylacetamide (Rosowsky et al., J. Med. Chem., 1985, 28, 660–667) is combined with synthetic FKBP ligand 2 (D. Holt et al., JACS, 1993, 115, 9925) with 2 equivalents of potassium tert-butoxide and stirred at room temperature for 24–48 h. The reaction is monitored by thin layer chromatography (TLC, 9/1 chloroform/methanol). When the reaction is complete, the solvent is removed under reduced pressure, and the product is purified using silica gel chromatography with 19/1 chloroform/methanol as eluent to provide the desired bifunctional molecule 3.

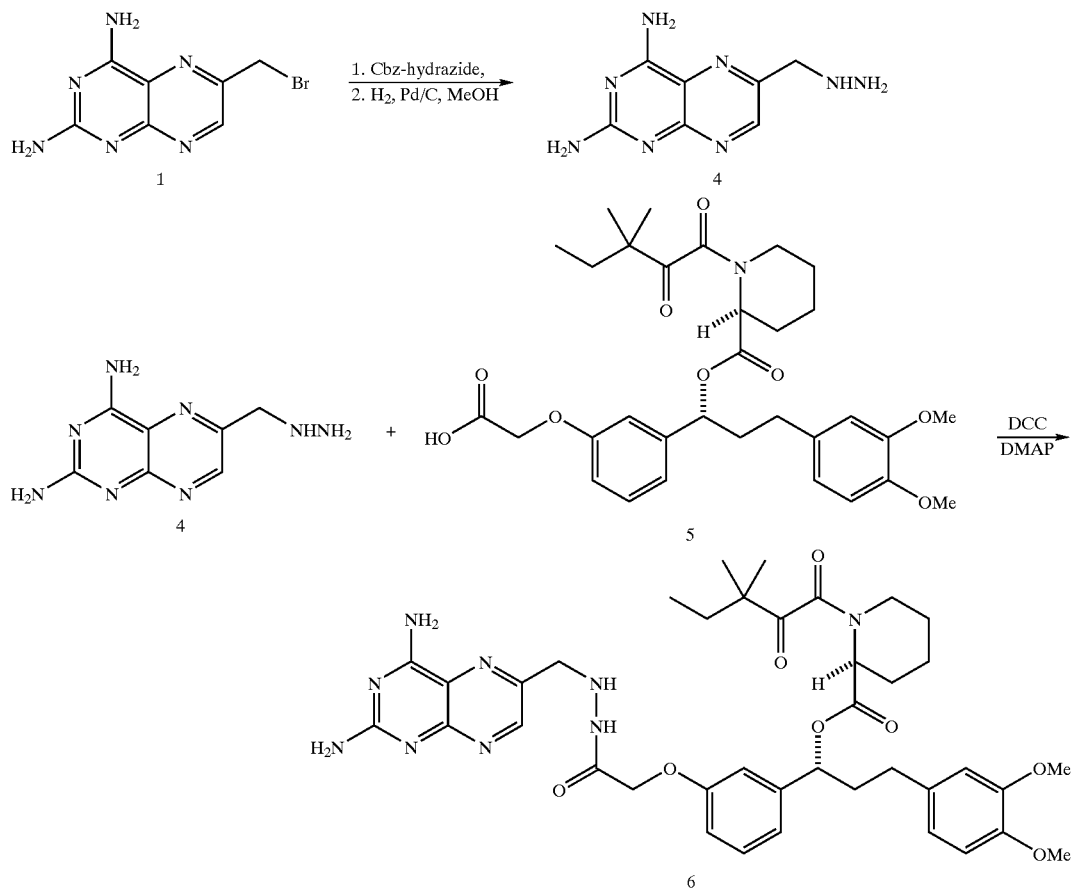

EXAMPLE 2

A solution of 2,4-diamino-6-bromomethylpteridine (1) (Rosowsky, et al.) is dissolved in dimethylacetamide and combined with 1 equivalent of carbobenzoxyhydrazide and 1 equivalent of barium oxide and stirred under an argon atmosphere at 46° C. for 24 h. The reaction is monitored by TLC with 9/1 chloroform/methanol and purified directly using silica gel chromatography with 9/1 chloroform/methanol as the eluent. The intermediate product is reduced using catalytic hydrogenation with 10% Pd/C catalyst and atmospheric hydrogen pressure in methanol. The reaction is monitored by TLC (4/1 chloroform/methanol) and product 4 is isolated by filtering the mixture through celite to remove the solid catalyst and removing methanol under reduced pressure. Product 4 is coupled to SLF (5) (Holt et al) using dicyclohexylcarbodiimide and catalytic DMAP in dimethylformamide. The reaction is monitored by TLC (19/1 chloroform/methanol) and product 6 is isolated using silica gel chromatography (19/1 chloroform/methanol as eluent).

C. Assays

In vitro Assay

The resulting bifunctional pteridine-FKBP ligand molecules are tested in an in vitro DHFR inhibition assay to select a molecule with the desired properties. The desired molecule fulfills the following requirements:

1. In a DHFR inhibition assay the desired pteridine-FKBP ligand bifunctional molecule inhibits the acitivity of DHFR in a concentration dependent manner. Molecules that are not able to inhibit DHFR efficiently are discarded. In these molecules, the linker between the pteridine and FKBP ligand affects the activity of the pteridine.

2. When the in vitro DHFR inhibiton assay is repeated in the presence of increasing concentrations of FKBP, the ability of the desired pteridine-FKBP ligand molecule to inhibit DHFR is decreased in correlation to increasing FKBP concentrations. Pteridine-FKBP ligand molecules, which can inhibit DHFR despite FKBP, are discarded because the linkers of these molecules interfere with bifunctional molecule binding to FKBP or the linkers do not support steric clashes between the FKBP and DHFR surfaces.

3. The activity reduction of the desired pteridine-FKBP ligand bifunctional molecule in the presence of FKBP is based on the binding to FKBP via the FKBP ligand moiety. To demonstrate this, the assay is repeated in the presence of pteridine-FKBP ligand bifunctional molecule, FKBP and increasing concentrations of FK506 which competes with the FKBP ligand moiety of bifunctional molecule for FKBP binding. As the concentration of FK506 is increased, the activity of pteridine-FKBP ligand bifunctional molecule is regained because FK506 replaces the ligand moiety as the ligand for FKBP. The free pteridine-FKBP ligand bifunctional molecule can again bind and inhibit the activity of DHFR.

The desired bifunctional molecule fulfills the three stated requirements. Its use as a selective inhibitor is demonstrated in the following cell based assays.

Bacterial Assay

The desired bifunctional molecule can inhibit DHFR activity in vivo. E. coli does not express FKBP and the cells have no other FKBP ligand (e.g. SLF or FK506) binding protein. When E. coli cultures are incubated with increasing concentrations of bifunctional molecule, the growth of the cultures is inhibited in a concentration dependent fashion. When these cells are transformed with a vector that allows the inducible expression of human FKBP, the bacteria become less sensitive to the bifunctional molecule when FKBP is expressed. To demonstrate that this detoxification of the bifunctional molecule is based on binding to FKBP, increasing concentrations of FK506 are added to the culture medium. FK506 competes with the bifunctional molecule for FKBP binding so that increasing concentrations of free bifunctional moelcule are present which can inhibit DHFR. FK506 by itself has no effect on the growth of the bacterial cultures in the presence or absence of FKBP.

This assay demonstrates that the presence of FKBP protects cells from the DHFR inhibitory activity of pteridine-FKBP ligand bifunctional molecules. This observation is the basis for creating cell selective anti-microbials that show reduced toxicity in humans.

It is evident from the above results and discussion that the subject invention provides a powerful tool for improving the affinity and/or specificity and selectivity of drugs. As such, the subject method provides for the improvement of drugs currently in use, e.g. by reducing unwanted side effects. Furthermore, the subject methods can be used to improve drugs that have, until now, been clinically useless due to considerable toxicity in humans and animals. Therefore, the invention provides for the potential usefulness of the variety of previously discovered and discarded biologically active compounds. Accordingly, the invention provides an important advancement in pharmacological science.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. In a method of administering a drug to a host in need of said drug, the improvement comprising:

administering to said host an effective amount of a bifunctional molecule of less than about 5000 daltons consisting of said drug or a fragment thereof linked to a ligand for a presenter protein endogenous to said host, wherein said drug binds to a drug target and said ligand binds to a presenter protein that is not said drug target.

2. The method according to claim 1, wherein said host is a mammalian host.

3. The method according to claim 2, wherein said mammalian host is human.

4. The method according to claim 1, wherein said drug is a small molecule.

5. The method according to claim 1, wherein said drug binds to an extracellular target.

6. The method according to claim 1, wherein said drug binds to an intracellular target.

7. The method according to claim 6, wherein said presenter protein ligand is a peptidyl prolyl isom rase.

8. The method according to claim 1, wherein said drug moiety and ligand of said bifunctional molecule are joined by a linking group.

9. A method for producing a tripartite complex in a mammalian host, said method comprising:

administering to said mammalian host an effective amount of a bifunctional molecule of less than about 5000 daltons consisting of a drug moiety linked to a ligand for a presenter protein endogenous to said mammalian host, wherein said drug moiety binds to a drug target and said ligand binds to a presenter protein that is not said drug target to produce said tripartite complex of said drug target, bifunctional molecule and presenter protein in said mammalian host.

10. The method according to claim 9, wherein said tripartite complex is produced intracellularly.

11. The method according to claim 9, wherein said tripartite complex is produced extracellularly.

12. The method according to claim 9, wherein said drug target is a protein.

13. The met hod according to claim 9, wherein said endogenous presenter protein is selected from the group consisting of: peptidyl-prolyl isomerases, Hsp90, steroid hormone receptors, cytoskeletal proteins, albumin and vitamin receptors.

14. The method according to claim 9, wherein said bifunctional molecule is administered as a pharmaceutical preparation.

15. The method according to claim 9, wherein said drug moiety and ligand of said bifunctional molecule are joined by a linking group.

16. A method for producing an intracellular tripartite complex in a mammalian host, said method comprising:

administering to said mammalian host an effective amount of a bifunctional molecule of less than about 5000 daltons comprising a drug moiety linked to a endogenous presenter protein ligand, wherein the said drug moiety and the said endogenous presenter protein ligand bind to different intracellular proteins; to produce said intracellular tripartite complex.

17. The method according to claim 16, wherein said endogenous presenter protein is selected from the group consisting of: peptidyl prolyl isomerases, Hsp90, steroid hormone receptors and cytoskeletal proteins.

18. The method according to claim 17, wherein said endogenous presenter protein is a peptidyl prolyl isomerase.

19. The method according to claim 16, wherein said drug moiety and ligand of said bifunctional molecule are joined by a linking group.

20. A method for enhancing the selectivity of a drug for an intracellular drug target in a first cell as compared to a second cell, containing the drug target said method comprising:

contacting said first and second cells with a bifunctional molecule of less than about 5000 daltons comprising said drug linked to a ligand for a presenter protein that is not said drug target present in said second cell but not in said first cell, wherein said drug binds to the drug target in said first cell and said ligand binds to the presenter protein in said second cell;

to produce a binary complex comprising said bifunctional molecule and presenter protein in said second cell wherein the drug does not bind to the drug target in the second cell, and to produce a binary complex comprising said bifunctional molecule and drug target in said first cell wherein the drug binds to the drug target in the first cell.

21. The method according to claim 20, wherein said drug is an antimicrobial agent.

22. The method according to claim 20, wherein said ligand is a peptidyl prolyl isomerase ligand.

23. The method according to claim 20, wherein said drug moiety and ligand of said bifunctional molecule are joined by a linking group.

* * * * *

UNITED STATES PATENT AND TRADEMARK OFFICE
CERTIFICATE OF CORRECTION

PATENT NO. : 6,921,531 B2
DATED : July 26, 2005
INVENTOR(S) : Briesewitz, Roger et al.

It is certified that error appears in the above-identified patent and that said Letters Patent is hereby corrected as shown below:

Title page,
Item [73], Assignee, "The Board of Trustees of the Leland Stanford Jr. University, Palo Alto, CA (US); The Howard Hughes Medical Institute, Chevy Chase, MD (US)" should be replaced with the assignee -- The Board of Trustees of the Leland Stanford Jr. University, Palo Alto, CA (US) --.

Column 38,
Lines 30 and 31, please delete the word "the".

Signed and Sealed this

Thirteenth Day of December, 2005

JON W. DUDAS
*Director of the United States Patent and Trademark Office*